(12) United States Patent
Bucciaglia et al.

(10) Patent No.: US 10,143,474 B2
(45) Date of Patent: Dec. 4, 2018

(54) SURGICAL STAPLER

(71) Applicant: Just Right Surgical, LLC, Louisville, CO (US)

(72) Inventors: Joseph D. Bucciaglia, Boulder, CO (US); Richard N. Granger, Niwot, CO (US); Allison B. Lyle, Boulder, CO (US); Robert E. Schneider, Erie, CO (US); Robert J. Smith, Louisville, CO (US)

(73) Assignee: Just Right Surgical, LLC, Louisville, CO (US)

( * ) Notice: Subject to any disclaimer, the term of this patent is extended or adjusted under 35 U.S.C. 154(b) by 18 days.

(21) Appl. No.: 15/148,744

(22) Filed: May 6, 2016

(65) Prior Publication Data

US 2016/0345971 A1    Dec. 1, 2016

Related U.S. Application Data

(60) Provisional application No. 62/159,191, filed on May 8, 2015.

(51) Int. Cl.
  *A61B 17/068*    (2006.01)
  *A61B 17/072*    (2006.01)
  *A61B 17/10*    (2006.01)

(52) U.S. Cl.
  CPC ...... *A61B 17/07207* (2013.01); *A61B 17/105* (2013.01); *A61B 2017/07214* (2013.01);
  (Continued)

(58) Field of Classification Search
  CPC ........... A61B 2017/07278; A61B 2017/07285; A61B 2017/07271
  See application file for complete search history.

(56) References Cited

U.S. PATENT DOCUMENTS 3,079,606 A    3/1963    Bobrov
3,490,675 A    1/1970    Green
(Continued)

FOREIGN PATENT DOCUMENTS

AU    5476586 A    9/1986
CA    2773414 A1    11/2012
(Continued)

OTHER PUBLICATIONS

Acquaviva, Laure, "International Search Report and Written Opinion re Application No. PCT/US2016/031280", dated Oct. 25, 2016, p. 22.
(Continued)

*Primary Examiner* — Andrew M Tecco
(74) *Attorney, Agent, or Firm* — Neugeboren O'Dowd PC

(57) ABSTRACT

A surgical stapler, a cartridge for a surgical stapler, a cutting mechanism for a surgical stapler, and a method of applying surgical staples in a patient are disclosed herein. The stapler may have an anvil movably coupled to a support jaw between a clamped configuration and a closed configuration. The cartridge may be configured to fit within an envelope diameter and to removably house a plurality of B-form staples, at least one of the plurality of B-form staples having a base length and a leg length, the leg length at least 53% of the envelope diameter. The cartridge may have slots shaped to house at least a second one of the plurality of staples at an angle oblique to the first one of the plurality of staples.

13 Claims, 29 Drawing Sheets

(52) U.S. Cl.
CPC ............ *A61B 2017/07221* (2013.01); *A61B 2017/07228* (2013.01); *A61B 2017/07257* (2013.01); *A61B 2017/07271* (2013.01); *A61B 2017/07278* (2013.01); *A61B 2017/07285* (2013.01)

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | deSalis et al. |
| 5,074,454 A | 12/1991 | Peteres |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,240,163 A | 8/1993 | Lamond et al. |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,462,546 A | 10/1995 | Rydell |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |

(56) References Cited

U.S. PATENT DOCUMENTS

| | | |
|---|---|---|
| 5,562,241 A | 10/1996 | Knodel et al. |
| 5,562,682 A | 10/1996 | Oberlin |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |

(56) References Cited

U.S. PATENT DOCUMENTS

| | | |
|---|---|---|
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,177 B2 * | 12/2003 | Truckai ............ A61B 18/1445 606/205 |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,763,993 B2 | 7/2004 | Bolduc et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,905,497 B2 | 6/2005 | Truckai et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |

(56) References Cited

U.S. PATENT DOCUMENTS

| | | |
|---|---|---|
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,731,073 B2 | 6/2010 | Wixey et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,502 B2 | 11/2010 | Walberg et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |

(56) References Cited

U.S. PATENT DOCUMENTS

| | | |
|---|---|---|
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,629 B2 | 5/2011 | Wixey et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,886 B2 | 8/2011 | Sonnenschein et al. |
| 8,006,887 B2 | 8/2011 | Marczyk |
| 8,007,505 B2 | 8/2011 | Weller et al. |
| 8,007,513 B2 | 8/2011 | Nalagathla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 * | 12/2011 | Knodel ............... A61B 17/072 227/175.1 |
| 8,070,035 B2 | 12/2011 | Holsten et al. |
| 8,070,036 B1 | 12/2011 | Knodel |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,151 B2 | 4/2012 | Ingmanson et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,558 B2 | 5/2012 | Sapienza |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,416 B2 | 7/2012 | Milliman et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,236,010 B2 | 8/2012 | Ortiz et al. |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,252,009 B2 | 8/2012 | Weller et al. |
| 8,256,656 B2 | 9/2012 | Milliman et al. |
| 8,267,300 B2 | 9/2012 | Boudreaux |
| 8,272,554 B2 | 9/2012 | Whitman et al. |
| 8,281,972 B2 | 10/2012 | Wixey et al. |
| 8,292,152 B2 | 10/2012 | Milliman et al. |
| 8,342,377 B2 | 1/2013 | Milliman et al. |
| 8,365,971 B1 | 2/2013 | Knodel |
| 8,453,913 B2 | 6/2013 | Milliman |
| 8,496,155 B2 * | 7/2013 | Knodel ............... A61B 17/072 227/175.1 |
| 8,517,240 B1 | 8/2013 | Mata et al. |
| 8,636,766 B2 | 1/2014 | Milliman et al. |
| 8,939,343 B2 | 1/2015 | Milliman et al. |
| 8,967,446 B2 | 3/2015 | Beardsley et al. |
| 8,998,951 B2 | 4/2015 | Knodel et al. |
| 9,016,541 B2 * | 4/2015 | Viola ............... A61B 17/072 227/176.1 |

(56) References Cited

U.S. PATENT DOCUMENTS

| | | |
|---|---|---|
| 9,027,817 B2 | 5/2015 | Milliman et al. |
| 9,089,326 B2* | 7/2015 | Krumanaker ........ A61B 17/072 |
| 9,144,427 B2 | 9/2015 | Knodel et al. |
| 9,265,500 B2 | 2/2016 | Sorrentino et al. |
| 9,510,827 B2* | 12/2016 | Kostrzewski ........ A61B 17/068 |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0232201 A1 | 11/2004 | Wenchell et al. |
| 2004/0243151 A1 | 12/2004 | Demmy et al. |
| 2004/0267310 A1 | 12/2004 | Racenet et al. |
| 2005/0103819 A1 | 5/2005 | Racenet et al. |
| 2005/0119669 A1 | 6/2005 | Demmy |
| 2005/0189397 A1 | 9/2005 | Jankowski |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0027469 A1 | 2/2007 | Smith et al. |
| 2007/0073341 A1 | 3/2007 | Smith et al. |
| 2007/0084897 A1 | 4/2007 | Shelton et al. |
| 2007/0084899 A1 | 4/2007 | Taylor |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0295780 A1 | 12/2007 | Shelton et al. |
| 2008/0023522 A1* | 1/2008 | Olson .............. A61B 17/07207 227/175.1 |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078808 A1 | 4/2008 | Hess et al. |
| 2008/0110961 A1 | 5/2008 | Voegele et al. |
| 2008/0149685 A1 | 6/2008 | Smith et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296344 A1 | 12/2008 | Cropper et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005808 A1 | 1/2009 | Hess et al. |
| 2009/0065549 A1 | 3/2009 | Viola |
| 2009/0078739 A1 | 3/2009 | Viola |
| 2009/0090763 A1 | 4/2009 | Zemlok et al. |
| 2009/0090766 A1 | 4/2009 | Knodel |
| 2009/0209946 A1 | 8/2009 | Swayze et al. |
| 2009/0209990 A1 | 8/2009 | Yates et al. |
| 2009/0236395 A1 | 9/2009 | Scirica |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277946 A1 | 11/2009 | Marczyk |
| 2009/0277949 A1 | 11/2009 | Viola et al. |
| 2009/0283568 A1 | 11/2009 | Racenet et al. |
| 2009/0306708 A1 | 12/2009 | Shah |
| 2009/0308907 A1 | 12/2009 | Nalagatla et al. |
| 2010/0012703 A1 | 1/2010 | Calabrese et al. |
| 2010/0012704 A1 | 1/2010 | Racenet et al. |
| 2010/0069942 A1 | 3/2010 | Shelton, IV |
| 2010/0072254 A1 | 3/2010 | Aranyi et al. |
| 2010/0076429 A1 | 3/2010 | Heinrich |
| 2010/0076459 A1 | 3/2010 | Farascioni |
| 2010/0089970 A1 | 4/2010 | Smith et al. |
| 2010/0127041 A1 | 5/2010 | Morgan et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0147921 A1 | 6/2010 | Olson |
| 2010/0147922 A1 | 6/2010 | Olson |
| 2010/0155453 A1 | 6/2010 | Bombard et al. |
| 2010/0170931 A1 | 7/2010 | Viola |
| 2010/0191255 A1 | 7/2010 | Crainich et al. |
| 2010/0193566 A1 | 8/2010 | Scheib et al. |
| 2010/0224668 A1 | 9/2010 | Fontayne et al. |
| 2010/0230468 A1 | 9/2010 | Viola |
| 2010/0237130 A1 | 9/2010 | Scirica |
| 2010/0243709 A1 | 9/2010 | Hess et al. |
| 2010/0249802 A1 | 9/2010 | May et al. |
| 2010/0252611 A1 | 10/2010 | Ezzat et al. |
| 2010/0252612 A1 | 10/2010 | Viola |
| 2010/0264192 A1 | 10/2010 | Marczyk |
| 2010/0264193 A1 | 10/2010 | Huang et al. |
| 2010/0264194 A1 | 10/2010 | Huang et al. |
| 2010/0294828 A1 | 11/2010 | Bindra et al. |
| 2010/0294829 A1 | 11/2010 | Giordano et al. |
| 2010/0301095 A1 | 12/2010 | Shelton, IV et al. |
| 2010/0305552 A1 | 12/2010 | Shelton, IV et al. |
| 2010/0308100 A1 | 12/2010 | Boudreaux |
| 2010/0320252 A1 | 12/2010 | Viola et al. |
| 2010/0320254 A1 | 12/2010 | Zemlok et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036887 A1 | 2/2011 | Zemlok et al. |
| 2011/0036888 A1 | 2/2011 | Pribanic et al. |
| 2011/0036890 A1 | 2/2011 | Ma |
| 2011/0036891 A1 | 2/2011 | Zemlok et al. |
| 2011/0036892 A1 | 2/2011 | Marczyk et al. |
| 2011/0036895 A1 | 2/2011 | Marczyk et al. |
| 2011/0042439 A1 | 2/2011 | Johnson et al. |
| 2011/0042441 A1 | 2/2011 | Shelton, IV et al. |
| 2011/0046666 A1 | 2/2011 | Sorrentino et al. |
| 2011/0062213 A1 | 3/2011 | Scirica et al. |
| 2011/0068145 A1 | 3/2011 | Bedi et al. |
| 2011/0068148 A1 | 3/2011 | Hall et al. |
| 2011/0084114 A1 | 4/2011 | Marczyk et al. |
| 2011/0084115 A1 | 4/2011 | Bedi et al. |
| 2011/0087276 A1 | 4/2011 | Bedi et al. |
| 2011/0089221 A1 | 4/2011 | Masiakos et al. |
| 2011/0095067 A1 | 4/2011 | Ohdaira |
| 2011/0101067 A1 | 5/2011 | Johnson et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139851 A1 | 6/2011 | McCuen |
| 2011/0144640 A1 | 6/2011 | Heinrich et al. |
| 2011/0147433 A1 | 6/2011 | Shelton, IV et al. |
| 2011/0147434 A1 | 6/2011 | Hueil et al. |
| 2011/0155781 A1 | 6/2011 | Swensgard et al. |

(56) References Cited

U.S. PATENT DOCUMENTS

| | | | |
|---|---|---|---|
| 2011/0155784 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0155788 A1 | 6/2011 | Hillstead et al. |
| 2011/0163146 A1 | 7/2011 | Ortiz et al. |
| 2011/0163147 A1 | 7/2011 | Laurent et al. |
| 2011/0163149 A1 | 7/2011 | Viola |
| 2011/0163150 A1 | 7/2011 | Farascioni |
| 2011/0168757 A1 | 7/2011 | Viola et al. |
| 2011/0168760 A1 | 7/2011 | Viola et al. |
| 2011/0174862 A1 | 7/2011 | Shelton, IV et al. |
| 2011/0174863 A1 | 7/2011 | Shelton, IV et al. |
| 2011/0180585 A1 | 7/2011 | Czernik et al. |
| 2011/0186614 A1 | 8/2011 | Kasvikis |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0198385 A1 | 8/2011 | Whitman et al. |
| 2011/0198386 A1 | 8/2011 | Viola |
| 2011/0204119 A1 | 8/2011 | McCuen |
| 2011/0204120 A1 | 8/2011 | Crainich |
| 2011/0210157 A1 | 9/2011 | Knodel et al. |
| 2011/0215132 A1 | 9/2011 | Aranyi et al. |
| 2011/0215133 A1 | 9/2011 | Aranyi |
| 2011/0226837 A1 | 9/2011 | Baxter, III et al. |
| 2011/0233258 A1 | 9/2011 | Boudreaux |
| 2011/0233259 A1 | 9/2011 | Olson |
| 2011/0240713 A1 | 10/2011 | Scirica et al. |
| 2011/0240714 A1 | 10/2011 | Whitman et al. |
| 2011/0253765 A1 | 10/2011 | Nicholas et al. |
| 2011/0257679 A1 | 10/2011 | Ishitsuki et al. |
| 2011/0295282 A1 | 12/2011 | Glick et al. |
| 2012/0080332 A1 | 4/2012 | Shelton, IV et al. |
| 2012/0138660 A1 | 6/2012 | Shelton, IV |
| 2012/0168487 A1 | 7/2012 | Holsten et al. |
| 2012/0248169 A1 | 10/2012 | Widenhouse et al. |
| 2013/0087599 A1* | 4/2013 | Krumanaker ........ A61B 17/072 227/176.1 |
| 2013/0098969 A1* | 4/2013 | Scirica ............. A61B 17/07207 227/180.1 |
| 2013/0123822 A1 | 5/2013 | Wellman et al. |
| 2013/0146642 A1 | 6/2013 | Shelton, IV et al. |
| 2013/0253578 A1 | 9/2013 | Milliman |
| 2013/0306706 A1 | 11/2013 | Knodel |
| 2014/0033674 A1 | 2/2014 | Knodel et al. |
| 2014/0041191 A1 | 2/2014 | Knodel |
| 2014/0175146 A1 | 6/2014 | Knodel |
| 2014/0175147 A1 | 6/2014 | Manoux et al. |
| 2014/0175153 A1 | 6/2014 | Manoux et al. |
| 2014/0207165 A1 | 7/2014 | Knodel et al. |
| 2014/0263558 A1 | 9/2014 | Hausen et al. |
| 2014/0263559 A1 | 9/2014 | Williams et al. |
| 2014/0284372 A1* | 9/2014 | Kostrzewski ........ A61B 17/068 227/177.1 |
| 2014/0332578 A1 | 11/2014 | Fernandez et al. |
| 2014/0332580 A1 | 11/2014 | White et al. |
| 2014/0339286 A1 | 11/2014 | Motooka et al. |
| 2015/0012006 A1 | 1/2015 | Hausen et al. |
| 2015/0090766 A1 | 4/2015 | Milliman et al. |
| 2015/0119932 A1 | 4/2015 | Knodel |
| 2015/0209041 A1 | 7/2015 | Milliman et al. |
| 2015/0265277 A1 | 9/2015 | Knodel et al. |
| 2015/0374363 A1 | 12/2015 | Laurent, IV et al. |
| 2016/0000429 A1 | 1/2016 | Knodel |
| 2016/0249913 A1 | 9/2016 | Manoux et al. |

FOREIGN PATENT DOCUMENTS

| | | |
|---|---|---|
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 2090253 A2 | 8/2009 |
| EP | 2090254 A1 | 8/2009 |
| EP | 2583630 A2 | 4/2013 |
| EP | 2586378 A2 | 5/2013 |
| EP | 2586382 A2 | 5/2013 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 2048685 A | 12/1980 |
| GB | 2070499 A | 9/1981 |
| GB | 2141066 A | 12/1984 |
| GB | 2165559 A | 4/1986 |
| SU | 659146 A1 | 4/1979 |
| SU | 728848 A1 | 4/1980 |
| SU | 980703 A1 | 12/1982 |
| SU | 990220 A1 | 1/1983 |
| WO | 8302247 A1 | 7/1983 |
| WO | 8910094 A1 | 11/1989 |
| WO | 9210976 A1 | 7/1992 |
| WO | WO9308754 A1 | 5/1993 |
| WO | 9314706 A1 | 8/1993 |
| WO | WO2009071070 A2 | 6/2009 |
| WO | 2014107393 A1 | 7/2014 |

OTHER PUBLICATIONS

Moon, Kihwan, "International Preliminary Report on Patentability re Application No. PCT/US2013/077801", dated Jul. 16, 2015, p. 5, Published in: WO.

Lopez, Michelle, "Office Action re U.S. Appl. No. 13/952,630", dated Apr. 18, 2016, p. 24 Published in: US.

Krynski, William, "International Search Report and Written Opinion re Application No. PCT/US2013/77801", dated Mar. 3, 2014, p. 8 Published in: US.

(56) References Cited

OTHER PUBLICATIONS

Lopez, Michelle, "Office Action re U.S. Appl. No. 13/950,357", dated Jan. 22, 2016, p. 6 Published in: US.
Ratliff, Reginald A., "Response to Office Action re U.S. Appl. No. 13/950,357", dated Apr. 22, 2016, p. 7 Published in: US.
Lopez, Michelle, "Office Action re U.S. Appl. No. 13/950,357", dated Jun. 7, 2016, p. 5 Published in: US.
Ratliff, Reginald A., "Response to Office Action dated Jan. 22, 2016 re U.S. Appl. No. 13/950,357", dated Apr. 22, 2016, p. 13 Published in: US.
Acquaviva, Laure, "Invitation to Pay Additional Fees and Partial Search Report re Application No. PCT/US2016/031280", dated Jul. 26, 2016, p. 7.

\* cited by examiner

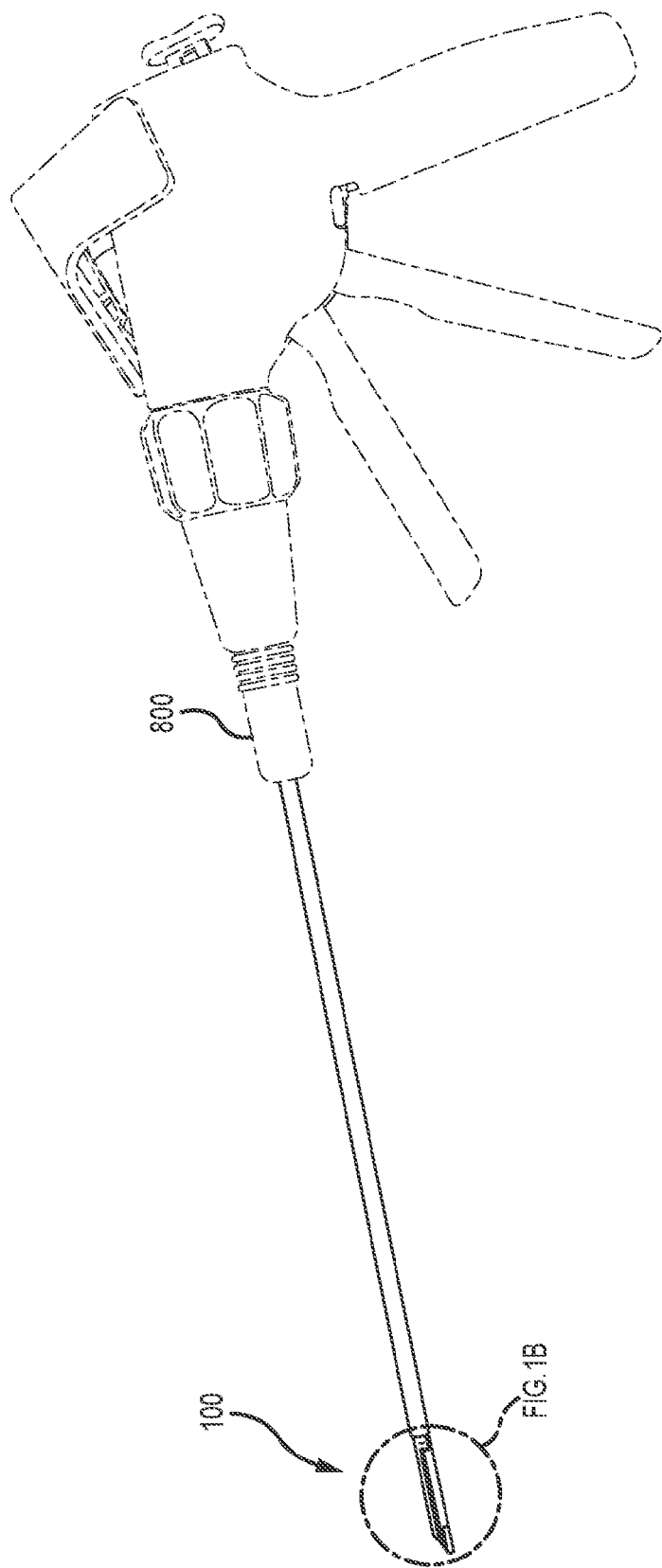

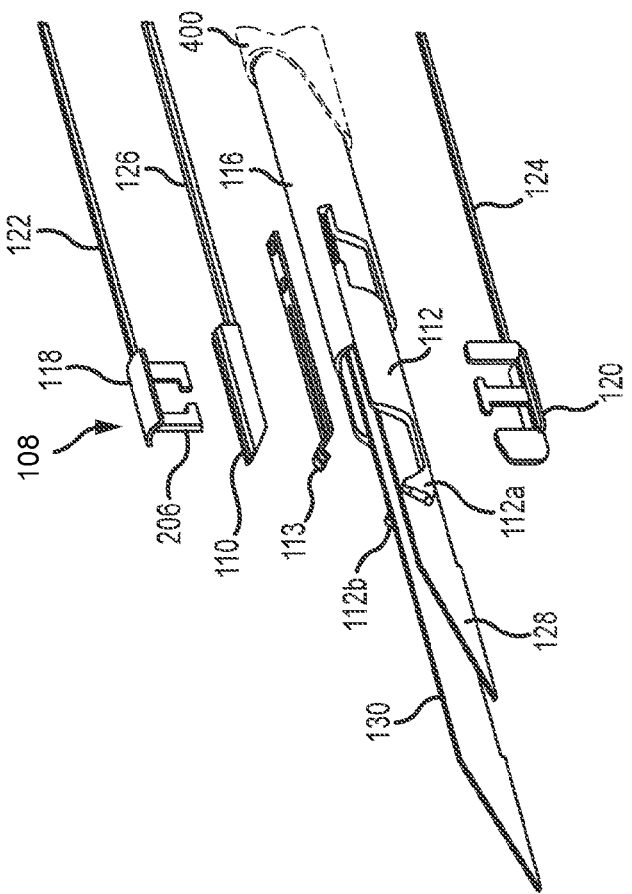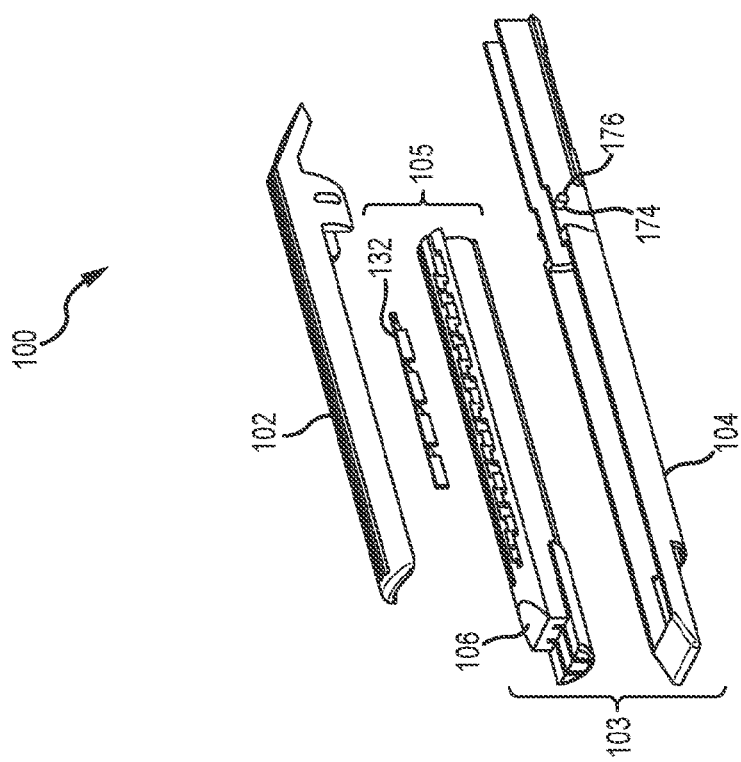
FIG.2

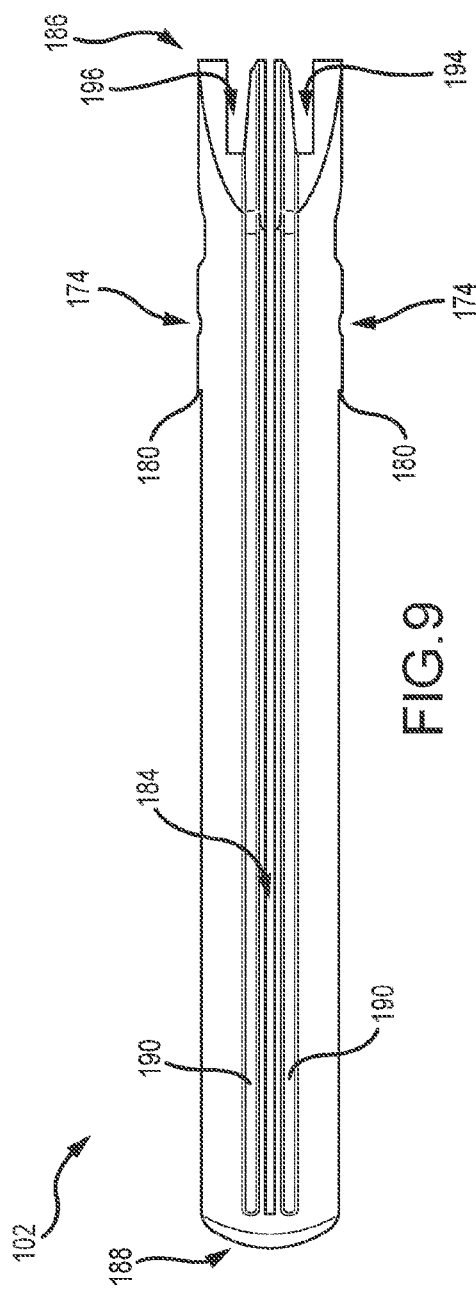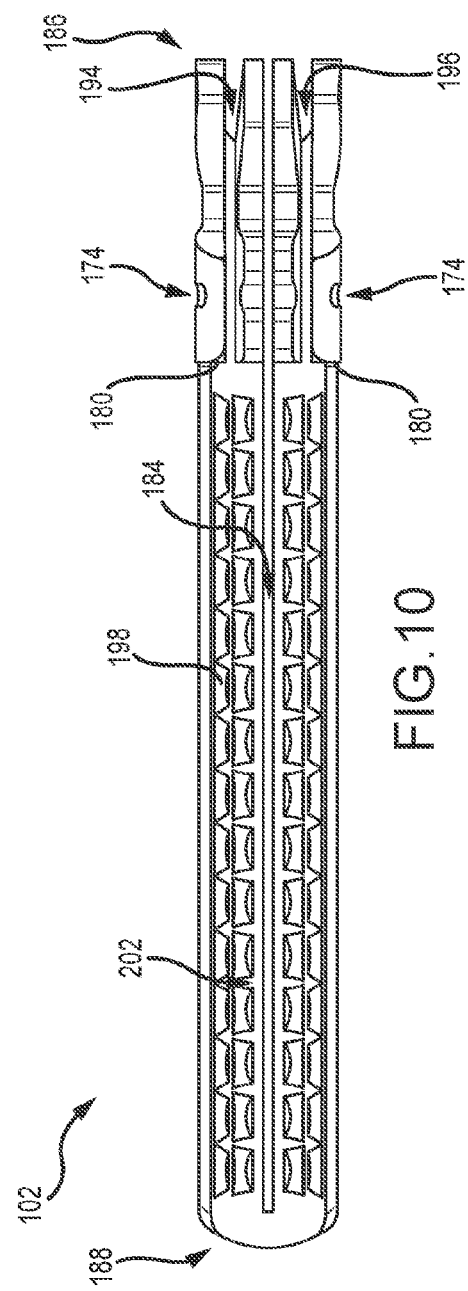

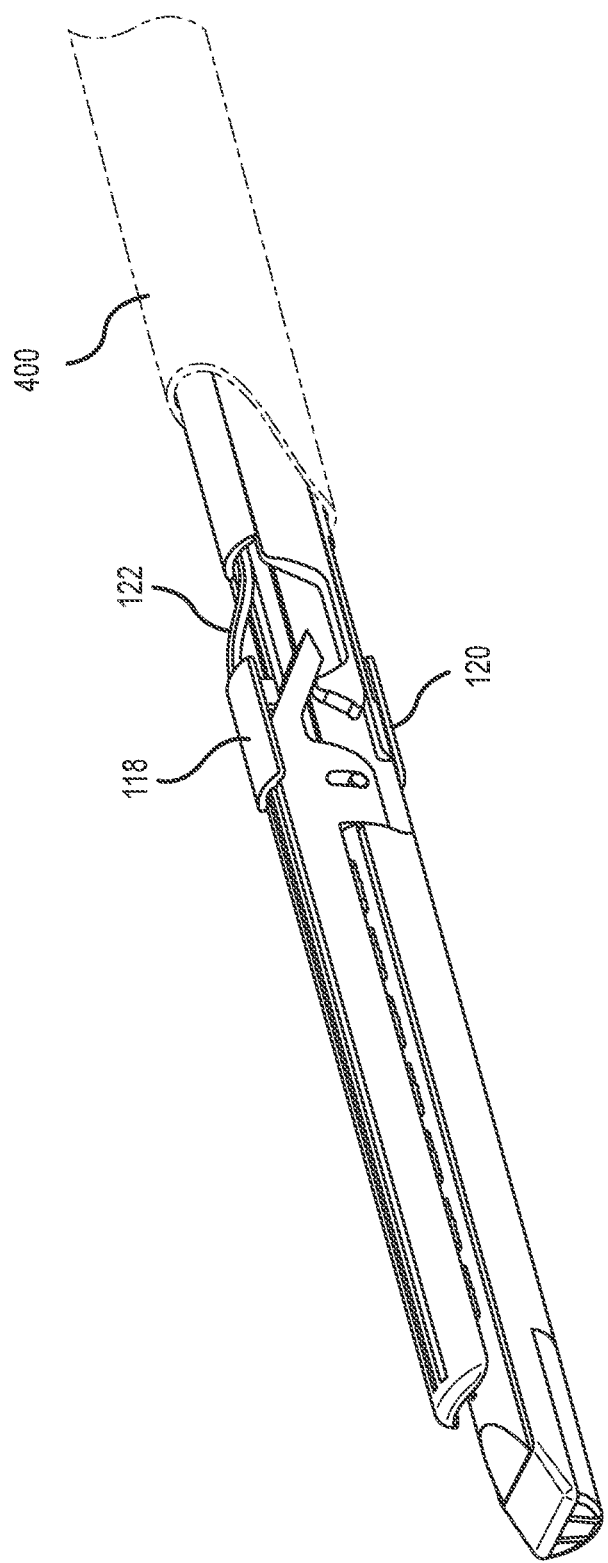

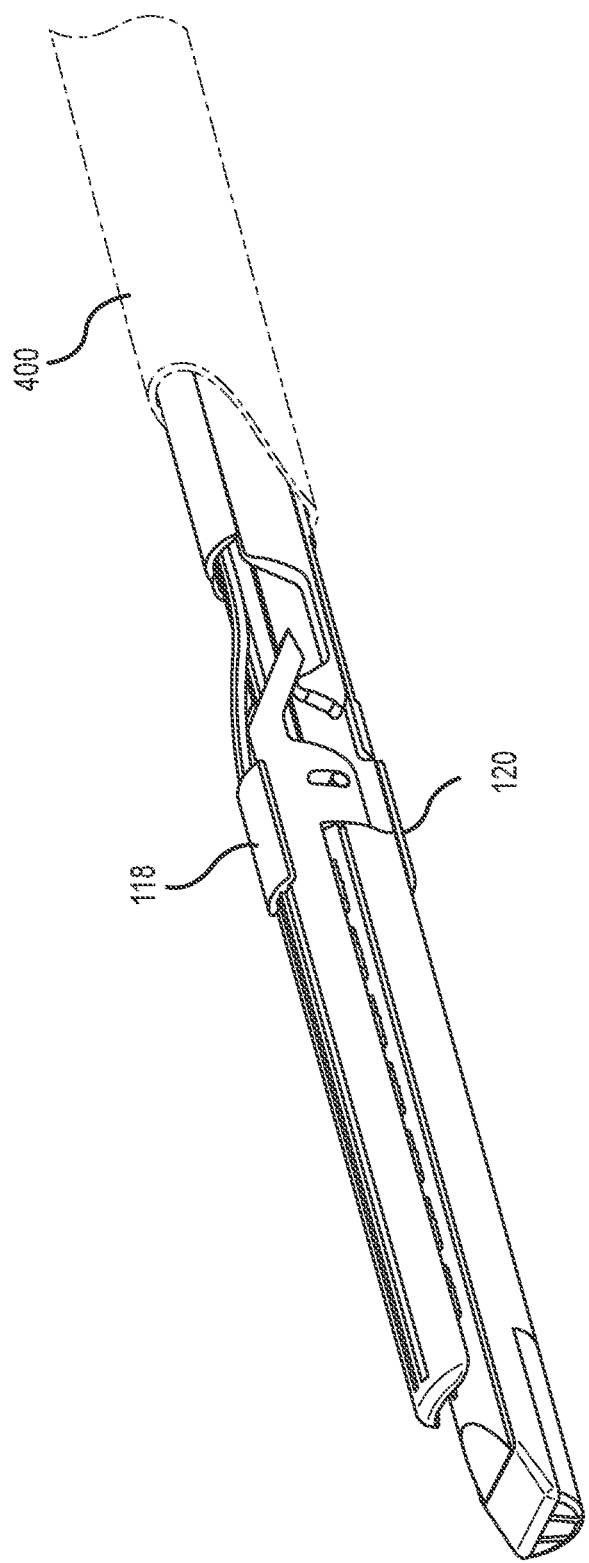

SURGICAL STAPLER

CROSS-REFERENCE TO RELATED APPLICATIONS

This application claims priority to U.S. Provisional Application No. 62/159,191, filed May 8, 2015 and entitled "SURGICAL STAPLER," the entire disclosure of which is hereby incorporated by reference for all proper purposes.

BACKGROUND

A surgical stapler is a medical device which is used to place surgical staples in a patient to close wounds ranging from bowel resections to skin incisions and others.

The staples to be applied to the tissue must be selected based on the thickness of the tissue to be stapled. Generally, larger staples require the use of surgical staplers that are also larger. For example, one 5 mm stapler sold under the trademark JustRight™, has a nominal shaft diameter of about 5 mm, and is currently indicated for applying staples having a nominal leg length of about 2 mm. Put another way, the 5 mm JustRight™ Surgical Stapler is indicated for use in procedures in which the tissue can be clamped between the stapler jaws to about 1 mm or less. JustRight™ is a trademark belonging to the assignee of this application.

Some currently-available staplers, such as a stapler sold under the trademarks Cardica™ MicroCutter Xchange® 30, do not use staples defined by a leg length; nonetheless, these staplers are similarly limited in that the staplers cannot staple tissue if the tissue cannot be clamped to a certain thickness. Should the surgeon need to staple tissue clamped to, for example, 2 mm, the surgeon would be required to use a stapler that is around 12 mm in diameter.

Some manufacturers have attempted to provide a relatively small stapler that may staple relatively thick tissue, such as the Cardica™ stapler described above. However, these staplers use what are known as D-shaped staples, as illustrated in FIGS. 35A-35B, instead of the more common B-form staples, which are illustrated in FIGS. 35C-35D. The D-shaped staples have relatively thick legs, with one of the legs not having a piercing feature, and have not been subject to extensive field use. It is believed by the Inventors that, for a given tissue thickness, the D-shaped staples introduce more trauma to the patient than do the B-form stapes.

While the use of a larger stapler for placing larger staples is often acceptable, in certain medical procedures, such as in procedures performed on small or weak patients, such as small children or those with physical or disease trauma, it may be desirable to use a relatively small shaft surgical device to staple tissue that is relatively thick, using a B-form staple.

Moreover, it is known that, if a surgeon clamps onto too much tissue for a given staple leg length or indicated use, currently-available staplers could still fire the staples and cut the tissue improperly. That is, the currently-available staplers could fire the staples, and thereafter cut the tissue, leaving the site open. It may therefore be desirable to provide a stapler that does not leave the site open or unsealed if the staples are not properly placed.

It may also be desirable to provide a surgeon the ability to create a wider cuff (that is, a larger tissue margin between the staples and transection line) for a given clamped tissue thickness than is possible using the currently-available surgical devices.

There therefore remains a need for a relatively small surgical stapler capable of stapling relatively thick tissue using B-form staples and/or providing a relatively wider cuff, with less impact to the patient, as well as other new and innovative features.

FIELD

The present disclosure relates generally to surgical instruments, and more specifically to endosurgical staplers and/or methods of placing surgical staples in a patient.

SUMMARY

In some examples, a cartridge for a surgical stapler is provided. The exemplary cartridge has an elongated body configured to fit within an envelope diameter and to removably house a plurality of B-form staples. At least one of the plurality of B-form staples has a base length and a leg length, the leg length at least 53% of the envelope diameter. The exemplary cartridge also has a tissue clamping interface, a first slot shaped to receive a translating cutting mechanism, and a second slot shaped to house at least a first one of the plurality of staples. The exemplary cartridge also has a third slot shaped to house at least a second one of the plurality of staples at an angle oblique to the first one of the plurality of staples.

In some examples, a surgical stapler is provided. The exemplary surgical stapler, has an anvil movably coupled to a support jaw between a clamped configuration, and a closed configuration wherein a tissue clamping interface in the anvil abuts a tissue clamping interface in the cartridge. The exemplary support jaw has a cartridge having an elongated body configured to removably house a plurality of B-form staples. At least one of the plurality of B-form staples has a base length and a leg length. The exemplary cartridge further comprises a first slot shaped to receive a translating cutting mechanism, a second slot shaped to house at least a first one of the plurality of staples, and a third slot shaped to house at least a second one of the plurality of staples at an angle oblique to the first one of the plurality of staples. The anvil and the support jaw comprising the cartridge are shaped to fit within an envelope diameter when in the closed configuration. The leg length of the at least one of the plurality of B-form staples is at least 53% of the envelope diameter in some examples.

In some examples, a method of placing a surgical staple in a patient is provided. The exemplary method includes providing a surgical stapler in a closed configuration, the stapler comprising an anvil movably coupled to a support jaw between a clamped configuration and a closed configuration wherein a tissue clamping interface in the anvil abuts a tissue clamping interface in the cartridge. The exemplary support jaw comprises a cartridge configured to removably house a plurality of B-form staples, at least one of the plurality of B-form staples having a base length and a leg length. The exemplary cartridge has a first slot shaped to receive a translating cutting mechanism, a second slot shaped to house at least a first one of the plurality of staples, and a third slot shaped to house at least a second one of the plurality of staples at an angle oblique to the first one of the plurality of staples. The exemplary anvil and support jaw comprising the cartridge are shaped to fit within an envelope diameter when in the closed configuration. The leg length of the at least one of the plurality of B-form staples is at least 53% of the envelope diameter in some examples. The exemplary method also includes passing at least a portion of the stapler in the closed configuration through an envelope diameter, and positioning tissue between the anvil and the support jaw. The exemplary method also includes moving the anvil to the clamped configuration wherein the anvil and the support jaw clamp the tissue between the anvil and the support jaw. The exemplary method also includes causing the stapler to form the plurality of staples about the tissue.

In some examples, a surgical stapler is provided. The exemplary stapler has a translating cutting mechanism having a first member having a cutting portion, and a second member. The exemplary cutting mechanism is movable between a collapsed configuration wherein the cutting mechanism is shaped to fit within the envelope diameter and an expanded configuration wherein the cutting mechanism does not fit within the envelope diameter.

BRIEF DESCRIPTION OF THE DRAWINGS

FIG. 1A is a perspective view of a surgical stapler coupled to an actuator;
FIG. 2 is an exploded perspective view of the surgical stapler in FIG. 1B;
FIG. 8A is a side view of the stapler with a linkage mechanism;
FIG. 8B is a detailed section view of the stapler in FIG. 8A;
FIG. 9 is a top view of the anvil in FIG. 8;
FIG. 10 is a bottom view of the anvil in FIG. 8;
FIG. 20B is a perspective view of the stapler in FIG. 1B;
FIG. 20C is a perspective view of the stapler in FIG. 1B.

DETAILED DESCRIPTION

Figure 1B:
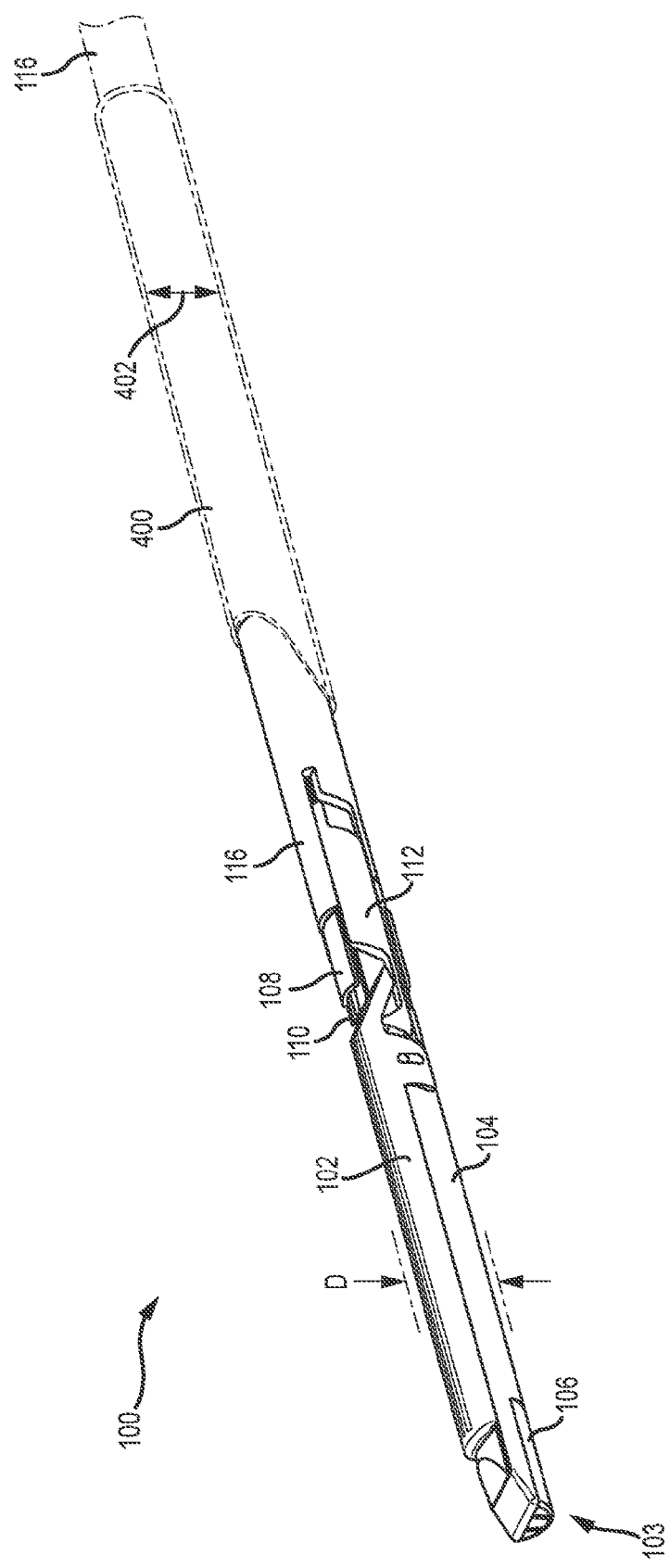
FIG. 1B is a perspective view of the surgical stapler in FIG. 1A.

To meet the previously-described needs, and/or to provide other new and useful features, a surgical stapler and method may be provided, and this paragraph is intended to be a conceptual overview, so as to give the reader a better understanding of the detailed description that follows. In some examples, a surgical stapler having a relatively small size is provided, and configured to place relatively large staples in a patient. This may be achieved by housing the staples at an oblique angle relative to each other or a common datum, such as a longitudinal axis or transection line. That is, instead of housing the staples parallel to each other (and/or perpendicular to a flat tissue clamping interface), as is known in the art, the Inventors provide, in some examples, a system in which the staples may be housed at a non-zero angle relative to each other or a common datum, and directed to staple tissue clamped between a curved jaw/cartridge and a curved anvil. This configuration gives surgeons the previously-unavailable option of placing relatively large staples using a relatively small stapler. Put another way, this configuration gives surgeons the previously-unavailable option of stapling tissue using a device gap of more than 1.0 mm using a 5 mm stapler (nominal).

For the purpose of this document, the term "nominal" shall refer to a range of dimensions usual in the medical device and/or surgical stapler industry at the time of invention or at the time of manufacture, whichever range is greater. For example, currently-available 5 mm staplers (nominal) are known to vary across manufacturers from 5.0 to 6.0 mm or 5.5+/−0.5 mm. As another example, a cannula having a nominal inner diameter of 5.5 mm is known to have an actual inner diameter of at least 5.59 mm as of the time of this writing, but may be greater as of the time of manufacture. A staple having a nominal leg length of 3.5 mm is known to have an actual leg length that varies by about +/−0.08 mm as of the time of this writing. Further, for the purpose of this document, all absolute terms, such as, for example, flat, parallel, perpendicular, round, etc., as well as all dimensions, shall be understood to include the limitation "within reasonable manufacturing tolerances at the time of the invention or at the time of manufacture, whichever are greater". For the purpose of this document, the term "proximal" shall refer to that portion or region of an instrument that is positioned closer to an intended user, such as a surgeon, and the term "distal" shall refer to the end or region away from the user or surgeon.

Turning now to FIG. 1, it illustrates an exemplary endosurgical stapler 100 passing through a cannula 400 in a manner known in the art and coupled to a stapler actuator 800. The interior diameter of the cannula 400 may be a nominal diameter of 5.0 mm or 5.5 mm, which may be up to 6.0 mm with manufacturing tolerances or standards known in the art. Those skilled in the art will understand that the cannula 400 is placed in the patient to provide a port through which the surgeon may access the patient using the stapler 100. The stapler 100 may have an anvil 102 that is configured to open or close relative to a support jaw 103. The support jaw 103 may include a cartridge housing 104, which houses a cartridge 106. In some embodiments, the housing 104 and cartridge 106 may be a unitary feature referenced as a support jaw 103. The anvil 102 and support jaw 103 may be coupled to or manipulated at a proximal region by way of a shaft 116 that houses actuators and/or other control mechanisms in a manner substantially as is known in the art.

To operate the anvil 102, an upper anvil positioner 110 and a lower anvil positioner 112 may be provided. The anvil positioners 110, 112 may operate to move the anvil 102 between an open position, a clamped position, and a closed position in a coordinated manner, and as will be described in further detail in subsequent sections of this document (see e.g. FIGS. 15-17).

Continuing with FIG. 1, a cutting mechanism 108 may be provided and movable relative to the distal portion of the stapler 100, to cut stapled tissue held between the anvil 102 and the support jaw 103 in a manner to be described in further detail in subsequent sections.

Those skilled in the art will readily appreciate that the components of the stapler 100 in FIG. 1 can be manufactured from any number of suitable materials, and, more particularly, that the materials must be selected with a suitable strength so as to withstand the forces required to clamp and staple relatively large bands of tissue using relatively small features. For example, any number of engineering materials, including, but not limited to, high-strength surgical steels, ceramics, and/or polymers may be selected.

In some embodiments, the surgical stapler 100 may have a housing 104, a portion thereof having an envelope diameter of about 5.5 millimeters or configured to pass through a 5.5 mm cannula 400.

In some embodiments, a 5.5 mm nominal housing 104 may house or carry a staple having a 3.0 mm nominal leg length in a manner as previously described herein. In some embodiments, the staple has a 4.8 mm nominal leg length. In some embodiments, the staple has a 2.0 mm nominal leg length. In some embodiments, the staple has a 2.5 mm nominal leg length.

Turning now to FIG. 2, further details of the stapler 100 in FIG. 1 are illustrated in an exploded perspective view. As can be appreciated, the cartridge 106 may be configured to house one or more staple pushers 132 such that, upon being actuated by one or more cams 128, 130, the staple pushers 132 may guide one or more staples (not illustrated in FIG. 2) out of the cartridge 106 and towards the anvil 102, whereby the staples are formed about tissue clamped between the anvil 102 and the cartridge 106/support jaw 103.

Figure 5:
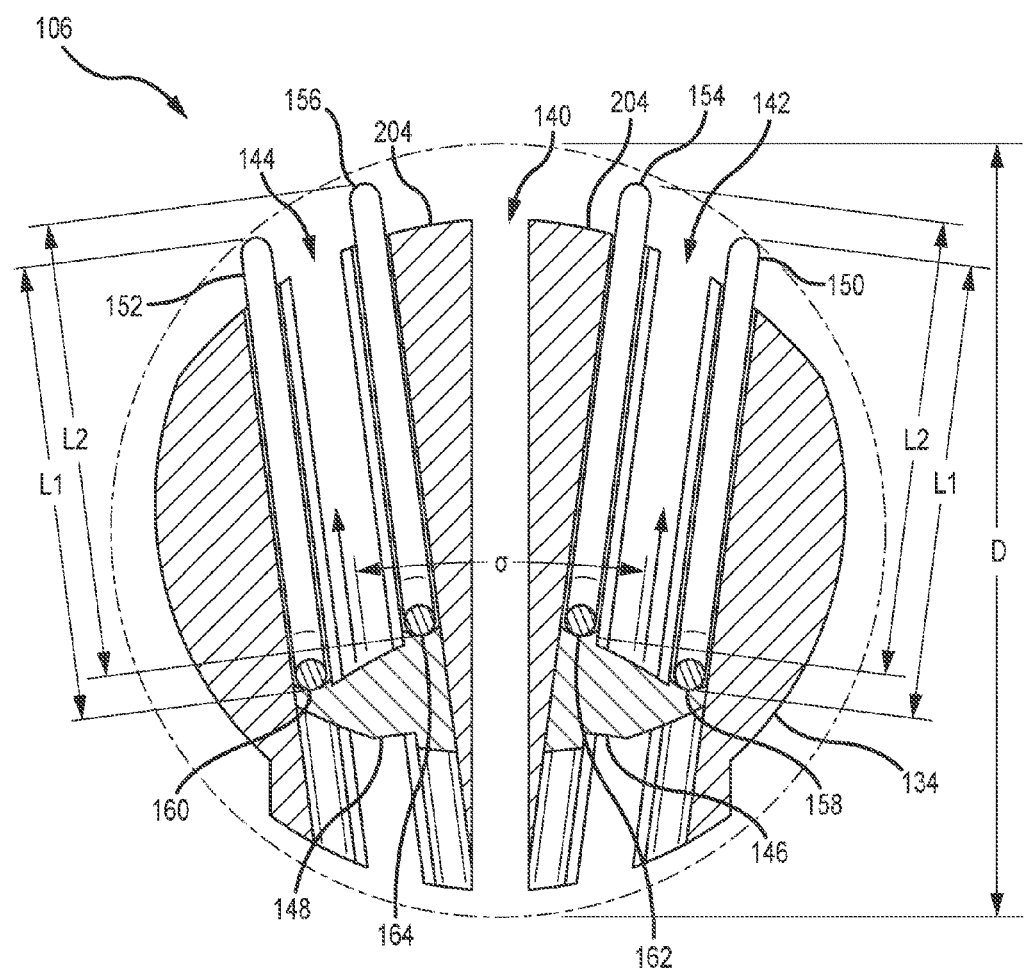
FIG. 5 is another cross-section view of the cartridge in FIG. 3.

The cam(s) 128, 130 may be actuated in a manner that is known to those skilled in the art. That is, in some embodiments, a standard staple pusher and staple driving concept as is currently available is used. In some embodiments, an extended cam and a reduced-size staple pusher may be provided. An extended cam is a cam that is taller than is historically used in surgical staplers of comparable size. An extended cam is therefore taller, to drive relatively large staple(s), such as staples having a leg length of 3.0 mm or greater, but the staple pusher size is of a reduced size such that the leg length of the staple(s) is greater than the pusher height, as is illustrated in FIG. 5. Those skilled in the art will recognize that, where the staple(s) 150 or staple pusher(s) 132 are housed at an oblique angle θ relative to each other or to a transection line, the cam(s) 128, 130 are at a similarly defined angle.

Returning to FIG. 2, the cutting mechanism 108 may have a first member 118 and a second member 120 that are movable or expandable relative to each other, and configured to move from a proximal region of the stapler 100 towards a distal region of the stapler 100 to cut tissue clamped by the stapler 100. The first member 118 of the cutting mechanism 108 may be actuated, controlled, and/or retracted using a first actuator 122, and the second member 120 of the cutting mechanism 108 may be actuated, controlled, and/or retracted using a second actuator 124.

The upper anvil positioner 110 may be actuated using an upper anvil actuator 126, and the lower anvil positioner 112 may be actuated using a lower anvil actuator (not illustrated). The lower anvil positioner 112 may have one or more flanges 112a, 112b configured to engage multiple surfaces of the anvil 102, to, in coordination with the upper anvil positioner 110, open, clamp, or close the anvil 102.

A spring 113 may be provided so as to maintain the anvil 102 biased towards the closed position even if the surgeon rotates the stapler 100 upside-down. That is, the spring 113 may prevent the anvil 102 from opening prior to intentional actuation, and may do so in a manner substantially as is known in the art.

Figure 3:
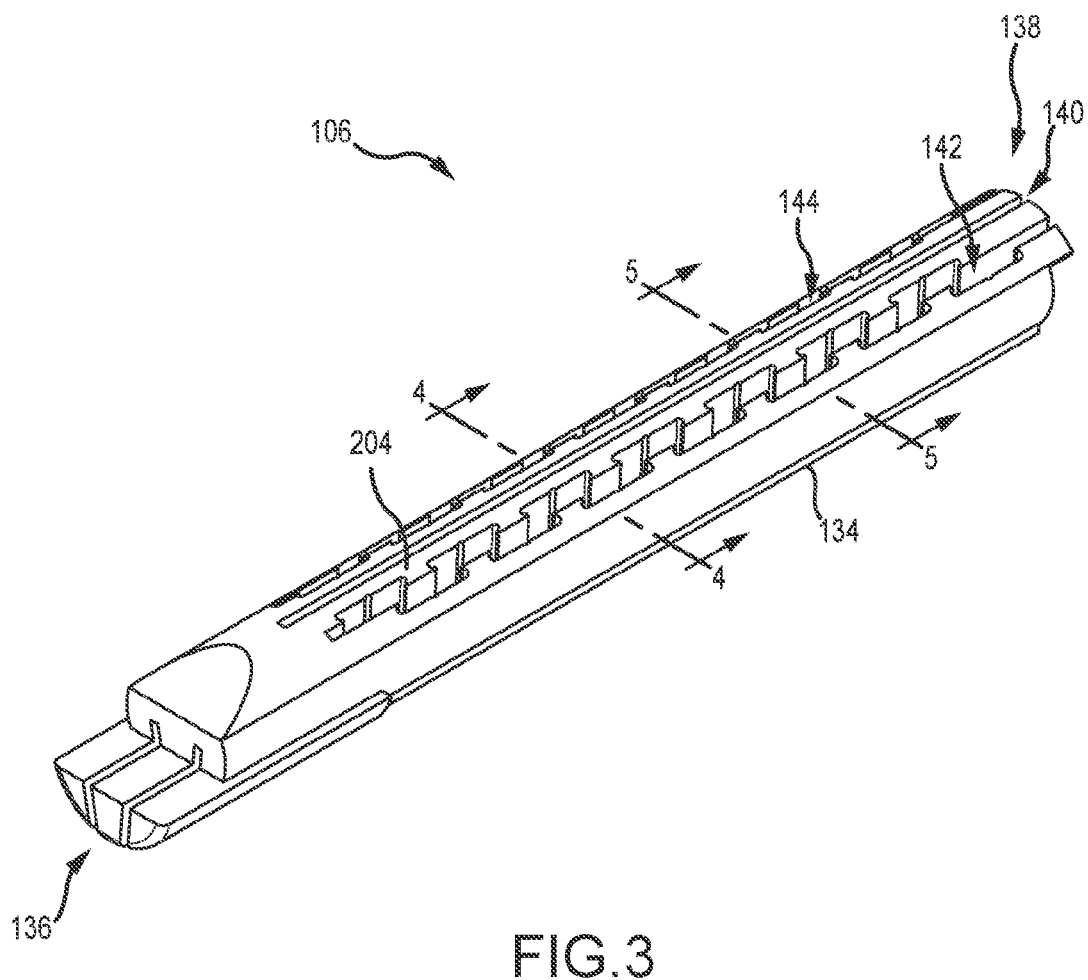
FIG. 3 is a perspective view of a cartridge in the stapler in FIG. 1B.

With reference now to FIG. 3, the cartridge 106 has an elongated body 134 having a distal end 136 and a proximal end 138. The cartridge 106 may be configured to removably house a plurality of staples (not illustrated in FIG. 3). A first slot 140 may be provided and shaped to receive a cutting mechanism (e.g. cutting mechanism 108 in FIG. 2) and/or to connect or receive a clamping or translating mechanism. With brief reference to FIGS. 1B and 21, a clamping mechanism may include a first member 118 or an upper flange 506 configured to apply a moving fulcrum force to the anvil 102 as the clamping mechanism 502 travels distally. In some embodiments, the clamping mechanism 502 is a cutting mechanism 108 or comprises a cutting portion 206. A second slot 142 shaped to house at least a first one of the plurality of staples, and a third slot 144 shaped to house at least a second one of the plurality of staples may also be provided.

Figure 4:
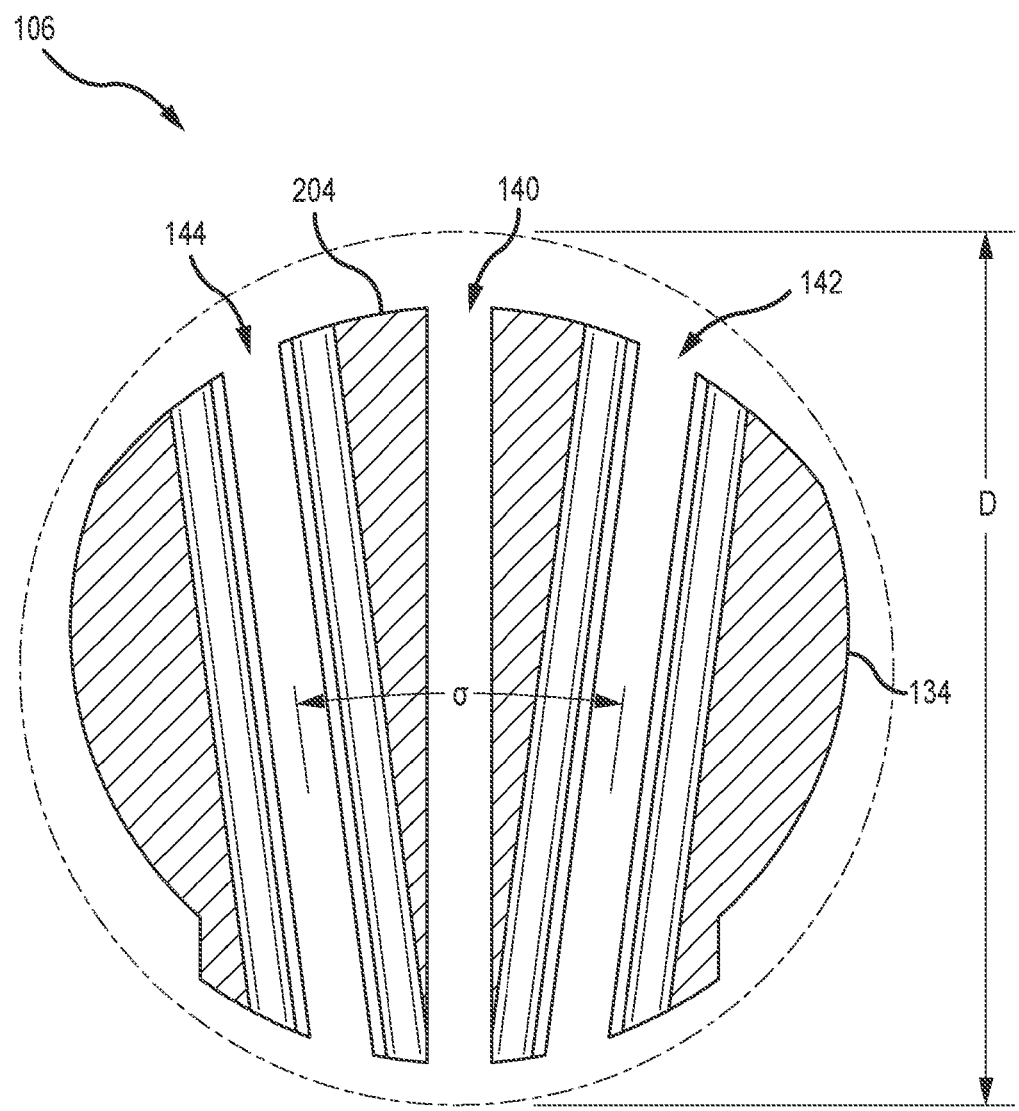
FIG. 4 is a cross-section view of the cartridge in FIG. 3.

As illustrated in FIG. 4, the second and third slots 142, 144 may be shaped, configured, or positioned so as to house the first staple at an angle θ oblique to the second slot or staple. In some embodiments, the angle θ between the second slot 142 and the third slot 144 is between about 4 degrees and about 30 degrees. In some embodiments, the angle θ is between about 10 degrees and about 20 degrees. In some embodiments, the angle θ is between about 10 degrees and about 15 degrees. In some embodiments, the angle θ is between about 15 degrees and about 20 degrees. In some embodiments, the angle θ is about 15 degrees plus or minus a suitable manufacturing tolerance. In some embodiments, the angle θ is between about 12 degrees and about 18 degrees.

As illustrated in FIG. 5, in some embodiments, the second slot 142 is shaped to translatably house at least a first staple pusher 146, and the third slot 144 is shaped to translatably house at least a second staple pusher 148. The second slot 142 and the third slot 144 may be configured to limit the first staple pusher 146 to translation at an angle θ oblique to a translation of the second staple pusher 148.

As is also apparent in FIG. 5, in some embodiments, the first staple pusher 146 may be configured to support a first staple 150 and a third staple 154, while the second staple pusher 148 may be configured to support a second staple 152 and a fourth staple 156. The first and third staples 150, 154 may be held substantially parallel to each other, while the second and fourth staples 152, 156 may be held substantially parallel to each other. The first and second staple pushers 146, 148 may be housed at an oblique angle θ relative to each other, and the cartridge 106 may be configured to limit translation of the staple pushers 146, 148 along relative paths that are oblique to each other.

The housing 104 or support jaw 103 may have an envelope diameter D of 5.6 mm or 5.5 mm, and may house or carry staples having a nominal leg length of 3.0 mm. In some embodiments, the housing 104 or support jaw 103 may house or carry a plurality of staples 150, 152, 154, 156 having a nominal leg length of 3.5 mm, as is illustrated in FIG. 5. The staples 150, 152, 154, 156 may be housed such that a first staple 150 and a second staple 152 are carried on opposing sides of a longitudinal axis defined by the housing 104, cartridge 106, or support jaw 103, or, as illustrated in FIG. 5, by a slot 140 for a cutting mechanism 108. The first and second staples 150, 152 may be angled relative to each other such that the legs of the first staple 150 and the legs of the second staple 152 form an angle θ with each other. The angle θ may be an acute angle θ in some embodiments. In some embodiments, the angle θ may be between about 4 degrees and about 30 degrees. In some embodiments, the staples 150, 152 may be mirrored on either side of the longitudinal axis or slot 140 such that the first staple 150 is rotated between about 2 degrees and about 15 degrees from a vertical orientation or from the slot 140, and the second staple 152 may be rotated in an opposing direction between about 2 degrees and about 15 degrees from the vertical orientation or slot 140. In some embodiments, the angle θ between the first staple 150 and the second staple 152 may be up to about 90 degrees. A third staple 154 may be parallel to the first staple 150, and a fourth staple 156 may be parallel to the second staple 152. The third and fourth staples 154, 156 may be closer to the longitudinal axis than are the first and second staples 150, 152.

It should be understood that the surgical stapler 100 may carry or house more than four staples. The first and second staples (and third and fourth staples if applicable) 150, 152, 154, 156 may be near a distal or working end of the surgical stapler 100, while another set of staples may be more proximal to the user. The staples 150, 152, 154, 156 may include a plurality of B-form staples in a staggered formation, so as to provide a suitable closing of tissue. That is, the staples may be in a formation wherein a distal leg of a proximal staple is positioned more distal than is a proximal leg of a distal staple, such that a portion of the proximal and distal staples are next to each other and a portion is not. Any suitable number of sets of staples may be provided.

Figure 6:
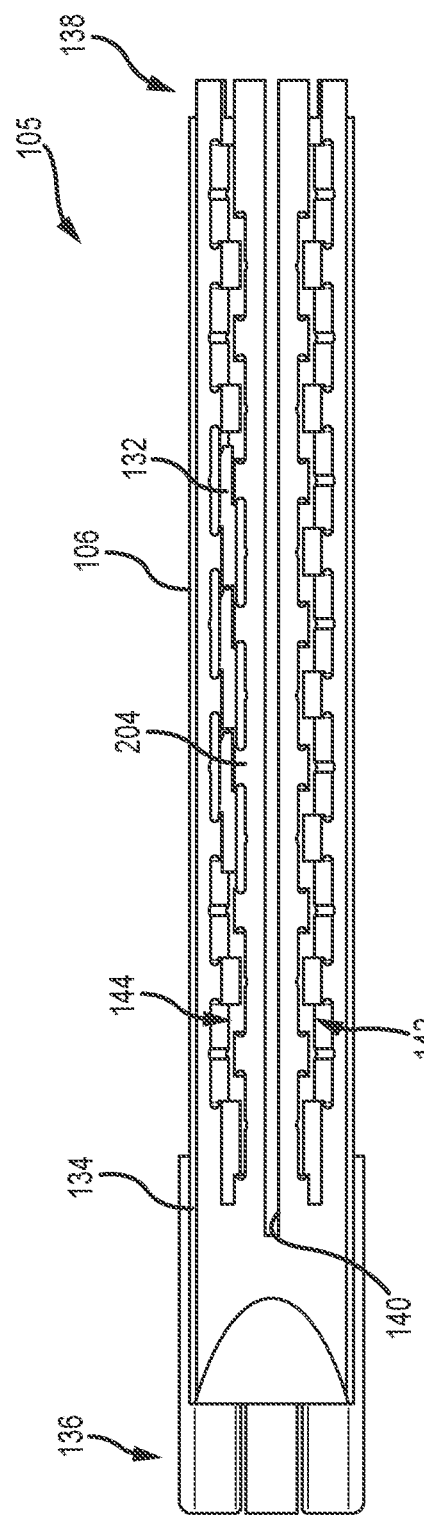
FIG. 6 is a top view of the cartridge in FIG. 3.
Figure 7:
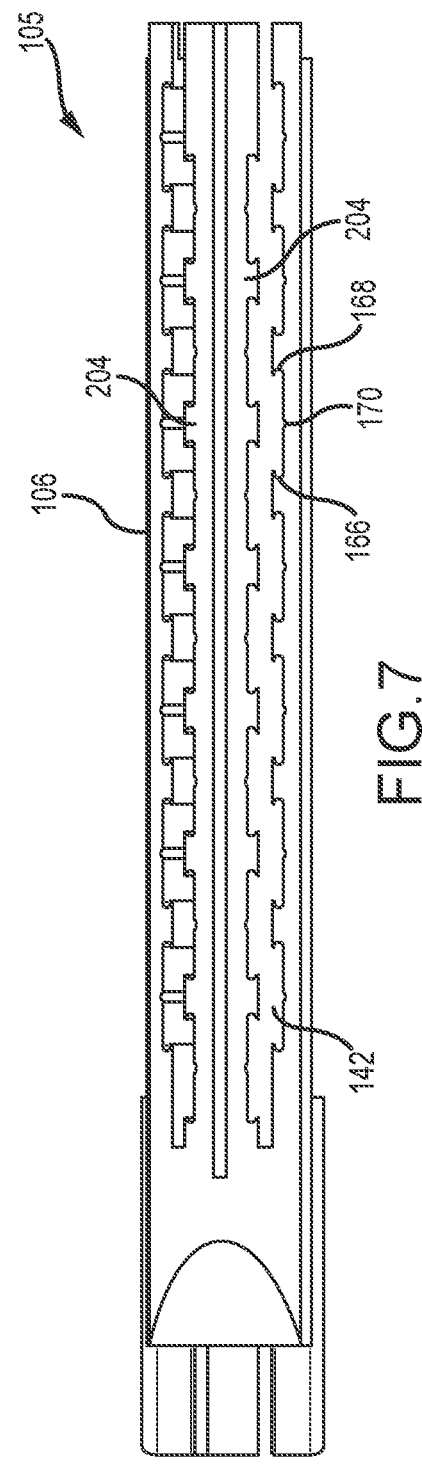
FIG. 7 is a rotated top view of the cartridge in FIG. 3.

With simultaneous reference now to FIGS. 5-7, in some embodiments, one or more of the staples 150, 152, 154, 156 are partially cupped or supported by a corner or features 166, 168, 170 in the second or third slots 142, 144. That is, cupped regions 158, 160, 162, 164 in the staple pusher(s) 146, 148 may partially support the staples 150, 152, 154, 156. In some embodiments, a cupped region 158 in a first staple pusher 146 may work in unison with a wall 170 and cupped regions 166, 168 in the elongated body 134 of the cartridge 106 to substantially limit a first staple 150 to translation as the first staple 150 is pushed by way of a cam (e.g. cam 128 in FIG. 2) and the first staple pusher (e.g. first staple pusher 146 in FIG. 5). Put another way, in some embodiments, a wall 170 and cupped regions 166, 168 in the cartridge 106 may provide primary support or guidance of the staple(s) 150, 152, 154, 156.

It should be understood that when referencing limiting a staple 150, 152, 154, 156 to translation, some lateral or rotational give or motion is generally acceptable. Although only two staple pushers 146, 148 are described herein, those skilled in the art will understand that any number of staple pushers 146, 148 may be provided, generally along two paths such as two slots 142, 144 that are on opposing sides of a slot 140 along which tissue is to be cut, so as to ensure tissue is stapled together on either side of the cut. The staple pushers 146, 148, slots 142, 144, and cartridge 106 may be configured to place the staples 150, 152, 154, 156 in two rows of staggered staples 150, 152, 154, 156 to ensure the stapled portion of the tissue is properly clamped and stapled shut across the entire transection length.

With continued reference generally to FIGS. 3-7, the cartridge 106 and/or stapler 100 may be configured to house or place staples 150, 152, 154, 156 in a patient, wherein at least one of the staples 150, 152, 154, 156 has a leg length of 3.42 mm or greater, or a nominal leg length of 3.5 mm or greater, and the anvil 102 and the support jaw 103 are configured to pass through a cannula 400 having an inner diameter of 5.6 mm or less or a nominal inner diameter of 5 mm or less. In some embodiments, at least one of the staples 150, 152, 154, 156 has a nominal leg length of 4.8 mm or greater or a leg length of 4.72 mm or greater, and the anvil 102 and the support jaw 103 are configured to pass through a cannula 400 having a nominal inner diameter of 8 mm or less or an inner diameter of 8.6 mm or less.

In some embodiments, the stapler 100 is configured to pass through a cannula 400 having an inner diameter 402, and the stapler 100 is simultaneously configured to carry at least first and second staples 150, 152 for placement in a patient, at least one of the staples 150, 152 having a leg length L that is at least 53% of the inner diameter 402 of the cannula 400, or at least 53% of an envelope diameter D of the stapler 100 when the stapler is in a closed configuration (see e.g. FIG. 1B).

In some embodiments, the leg length L is at least 58% of the inner diameter 402 or the envelope diameter D. In some embodiments, the leg length L is at least 60% of the inner diameter 402 of the cannula 400 or the envelope diameter D. In some embodiments, the leg length L is at least 61% of the inner diameter 402 of the cannula 400 or the envelope diameter D. For example, a staple 150 having a nominal leg length of 4.8 mm and a cannula 400 having a nominal inner diameter of 8.0 may have a ratio of 4.72/8.6 after taking into account manufacturing allowances. For example, a staple 150 having a nominal leg length of 4.8 mm and a cannula 400 having a nominal inner diameter of 8.0 may have a ratio of 4.88/8.0 at a less-than ideal tolerance stack-up.

In some embodiments, the leg length L is up to 62% of the inner diameter of the cannula 400 or the envelope diameter D. In some embodiments, the leg length L is up to 66% of the inner diameter 402 of the cannula 400 or the envelope diameter D. For example, a staple 150 having a nominal leg length of 3.5 mm and a cannula 400 having a nominal diameter of 5 mm may have a ratio of 3.58/5.0 at a less-than ideal tolerance stack-up. In some embodiments, the leg length L is between 55% and 67% of the inner diameter 402.

In some embodiments, the stapler 100 is configured to (a) pass through a cannula 400 having an inner diameter 402, (b) place at least first and second staples 150, 152 in a patient, each of the staples 150, 152 having a first leg length L1 that is between 55% and 67% of the inner diameter 402 of the cannula 400, and (c) place at least third and fourth staples 154, 156 in a patient, the third and fourth staples 154, 156 having a second leg length L2 that is different from the first leg length L1 of the first and second staples 150, 152. In some embodiments, the first leg length L1 is at least 57% of the inner diameter 402. In some embodiments, the first leg length is at least 58% of the inner diameter 402. In some embodiments, the first leg length is at least 61% of the inner diameter 402.

In some embodiments, the stapler 100 is configured to place a first staple 150 having a first leg length L1 and another staple 156 having a different leg length L2. In some embodiments, the stapler 100 is configured to place staples having a first leg length L1 on a first side of a tissue cut, and staples having a second leg length L2 on a second side of a tissue cut. In some embodiments, the stapler 100 is configured to place a first staple having a first leg length L1 and a second staple having a second leg length L2 on the same side of the tissue cut.

In some embodiments, the stapler 100 is configured with an outer envelope diameter D (see e.g. FIG. 1B) sized to pass through a cannula having an inner diameter 402 when the stapler 100 is in a closed configuration (see e.g. FIG. 15) wherein the curved interfaces 202, 204 abut one another. The stapler 100 may be configured to clamp tissue positioned between the anvil 102 and the support jaw 103 and compress the tissue to a particular thickness and/or to limit the tissue to a maximum particular thickness, herein referred to as a device gap G, between the anvil 102 and the cartridge 106 (see e.g. FIG. 14). Those skilled in the art will understand that surgical staplers 100 and the associated staples are generally sized according to the intended thickness of tissue to be stapled.

For the purpose of this document, the device gap G is defined as the maximum space allowed between the support jaw 103 or cartridge 106 and the anvil 102 at the time the device fires staple(s) 150 into tissue.

In one example, the stapler 100, if positioned about very thin tissue, may be configured to or allowed to "float" towards contact between the anvil 102 and support jaw 103 and then, as staple(s) 150 are fired into the tissue, the stapler 100 may be configured to allow the staple(s) 150 to bias or push the anvil 102 away from the cartridge 106, up to a maximum device gap G. The maximum device gap G may be limited to a distance defined by a translating cutting mechanism 108 (see e.g. FIGS. 14, 20C). The cutting mechanism 108 may move distally substantially or nearly simultaneously or in coordination with one or more cam(s) 128, 130, such as when the staple(s) 150 are fired, so as to prevent the stapler 100 from opening beyond the maximum device gap G.

Relatedly, and as another example, the stapler 100, if positioned about relatively thick tissue, may be configured to compress the tissue down to the maximum device gap G as the translating cutting mechanism 108 moves distally. For example, if the stapler 100 is configured to clamp tissue at a device gap G of 2.0 mm, and the tissue positioned between the stapler 100 is greater than 2.0 mm, the stapler 100 and/or cutting mechanism 108 may compress the tissue appropriately. Of note, if the tissue positioned between the anvil 102 and the support jaw 103 is so thick as to not be compressible to the appropriate device gap G, the cutting mechanism 108 may be configured to jam or stop translating into tissue that is not suitably clamped.

For example, most currently-available 5 mm (nominal) staplers are indicated for stapling tissue that can be clamped to less than 1.0 mm, while the Cardica 5 mm stapler (nominal—the actual size is greater than 5 mm, about 5.8 mm or more) is indicated for stapling tissue that can easily be clamped to 1.5 mm or less, and uses D-form staples. In both cases, if the surgeon wishes to staple tissue having a greater thickness, a larger stapler must be used. Relatedly, currently-available B-form staples having a nominal leg length of 3.5 mm are indicated for stapling tissue that can be clamped to between 1.5 mm and 2.0 mm. Currently-available B-form staples having a nominal leg length of 4.8 mm are indicated for stapling tissue that can be clamped to 2.0 mm.

In some embodiments, the envelope diameter D is about 5.5 mm or about 5.6 mm, and the device gap G is between about 0.75 mm and about 1.0 mm. In some embodiments, the envelope diameter D is about 5.5 mm or 5.6 mm, and the device gap G is between about 1.0 mm and about 1.5 mm. In some embodiments, the envelope diameter D is about 5.5 mm or 5.6 mm, and the device gap G is greater than about 1.5 mm, and up to about 2.0 mm. In some embodiments, the envelope diameter D is about 8.5 mm or 8.6 mm, and the device gap G is about 2.0 mm or greater.

In some embodiments, the device gap G is 13% of the envelope diameter D or greater. In some embodiments, the device gap G is 17% of the envelope diameter D or greater. In some embodiments, the device gap G is 20% of the envelope diameter D or greater. In some embodiments, the device gap G is 22% of the envelope diameter D or greater. In some embodiments, the device gap G is 26.8% of the envelope diameter D or greater. In some embodiments, the device gap G is 27.3% of the envelope diameter D or greater. In some embodiments, the device gap G is about 37% of the envelope diameter D or less. In some embodiments, the device gap G is between about 18% and about 37% of the envelope diameter D. In some embodiments, the device gap G is between about 22% and about 37% of the envelope diameter D. In some embodiments, the device gap G is between about 26.8% and about 35.7% of the envelope diameter D. In some embodiments, the device gap G is between 27.3% and about 36.4% of the envelope diameter D.

In some embodiments, the stapler 100 is modular, as illustrated in FIG. 2 or FIG. 6. That is, one or more interchangeable cartridge kits 105 may be provided. For example, a first cartridge kit 105 having a cartridge 106, one or more staple pushers 132, and one or more staples (not illustrated) having a first leg length may be interchangeable with a second cartridge kit 105 having a cartridge 106, one or more staple pushers 132, and one or more staples (not illustrated) having a second leg length that is different from the first leg length. In some embodiments, the cartridge kit(s) 105 is removable from a housing 104 or support jaw 103. In some embodiments, alignment features are provided in the housing 104, support jaw 103, and/or cartridge 106 to enable suitable alignment. In some embodiments, the cartridge kit 105 is removable from the support jaw 103 without the use of tools. In some embodiments, locking features may be provided in the cartridge kit 105 so as to prevent removal without the use of a tool. In some embodiments, the cartridge kit 105, housing 104, anvil 102, cutting mechanism 108, upper and/or lower anvil positioners 110, 112, and shaft 116 are removable as a unit from the stapler actuator 800.

Turning now to FIGS. 8-11, and as illustrated in FIG. 1, the stapler 100 may have an anvil 102. The anvil 102 may be shaped or configured to be movable relative to the support jaw 103, for example, by way of a linkage mechanism 172. The linkage mechanism 172 may include one or more recesses or passages 174 in one of the anvil 102 or the support jaw 103 (or the housing 104 in the support jaw 103), configured to engage with one or more corresponding protrusions 176 (see FIG. 2) in the other one of the anvil 102 or the support jaw 103 (or the housing 104 in the support jaw 103). The linkage mechanism 172 may be configured to limit the anvil 102 to rotation and translation relative to the support jaw 103 or housing 104. The linkage mechanism 172 may be configured to adjust a pivot point of the anvil 102 as the anvil 102 is rotated relative to the support jaw 103 or housing 104. FIGS. 8A and 8B illustrate how the linkage mechanism 172 may include one or more recesses or passages 174 in the support jaw 103 and one or more protrusions 176 in the anvil 102.

Figure 15:
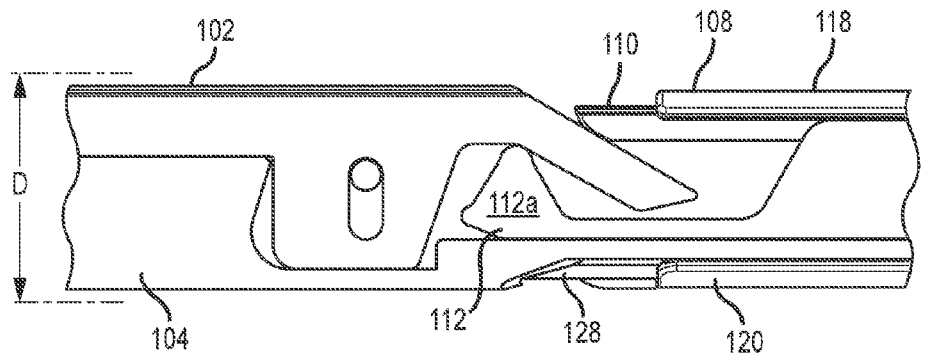
FIG. 15 is a side view of features of the stapler in FIG. 1B.
Figure 16:
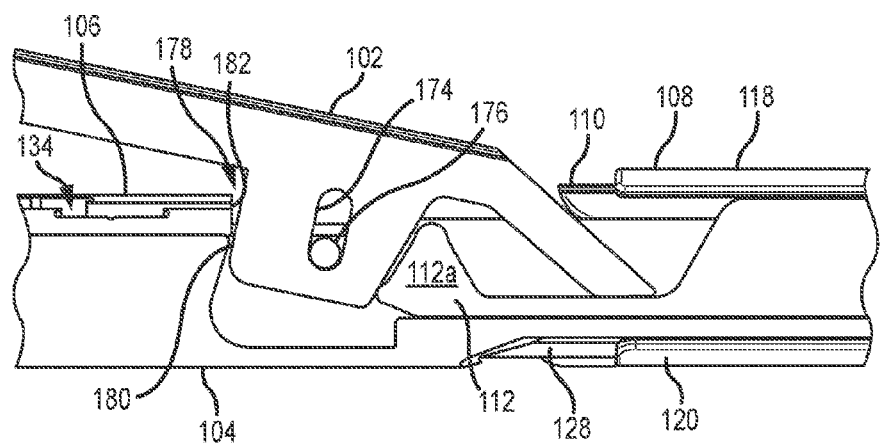
FIG. 16 is a side view of features of the stapler in FIG. 1B.
Figure 17:
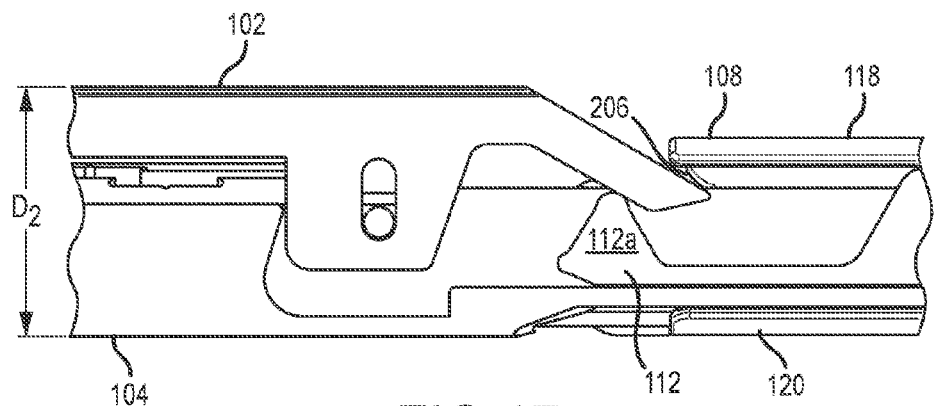
FIG. 17 is a side view of features of the stapler in FIG. 1B.

The linkage mechanism 172 may work in a coordinated manner with the upper and/or lower anvil positioners 110, 112 so as to effectuate, enable, and/or limit motion of the anvil 102 to movement between an open position, a clamped position, and a closed position (see e.g. FIGS. 15-17). Those skilled in the art will understand that, although the linkage mechanism 172 is illustrated as having a passage 174 in the anvil 102 and a protrusion 176 in the support jaw 103 or housing 104, any number of linkage mechanisms 172 may be employed.

In some embodiments, the linkage mechanism 172 includes a snap-fit between an elastic region of the anvil 102 and the support jaw 103 or housing 104. For example, the anvil 102 may have a slight protrusion on one or both sides that correspond to pits, passages, or recesses in the support jaw 103 or housing 104. During assembly, the anvil 102 may be caused to flex slightly, so as to snap-fit to the support jaw 103 or housing 104. In some embodiments, the elastic region may be created by a thin wall section in the anvil 102.

In some embodiments, one or more detents (not illustrated) may be provided in the anvil 102 and/or support jaw 103, and the detents may be configured to engage one or more recesses or passages in the other of the anvil 102 and/or support jaw 103, so as to enable assembly a tight fit between the anvil 102 and support jaw 103. A detent/recess/passage may be configured to allow a user, recycler, and/or manufacturer to disassemble the anvil 102 from the support jaw 103.

Figure 8:
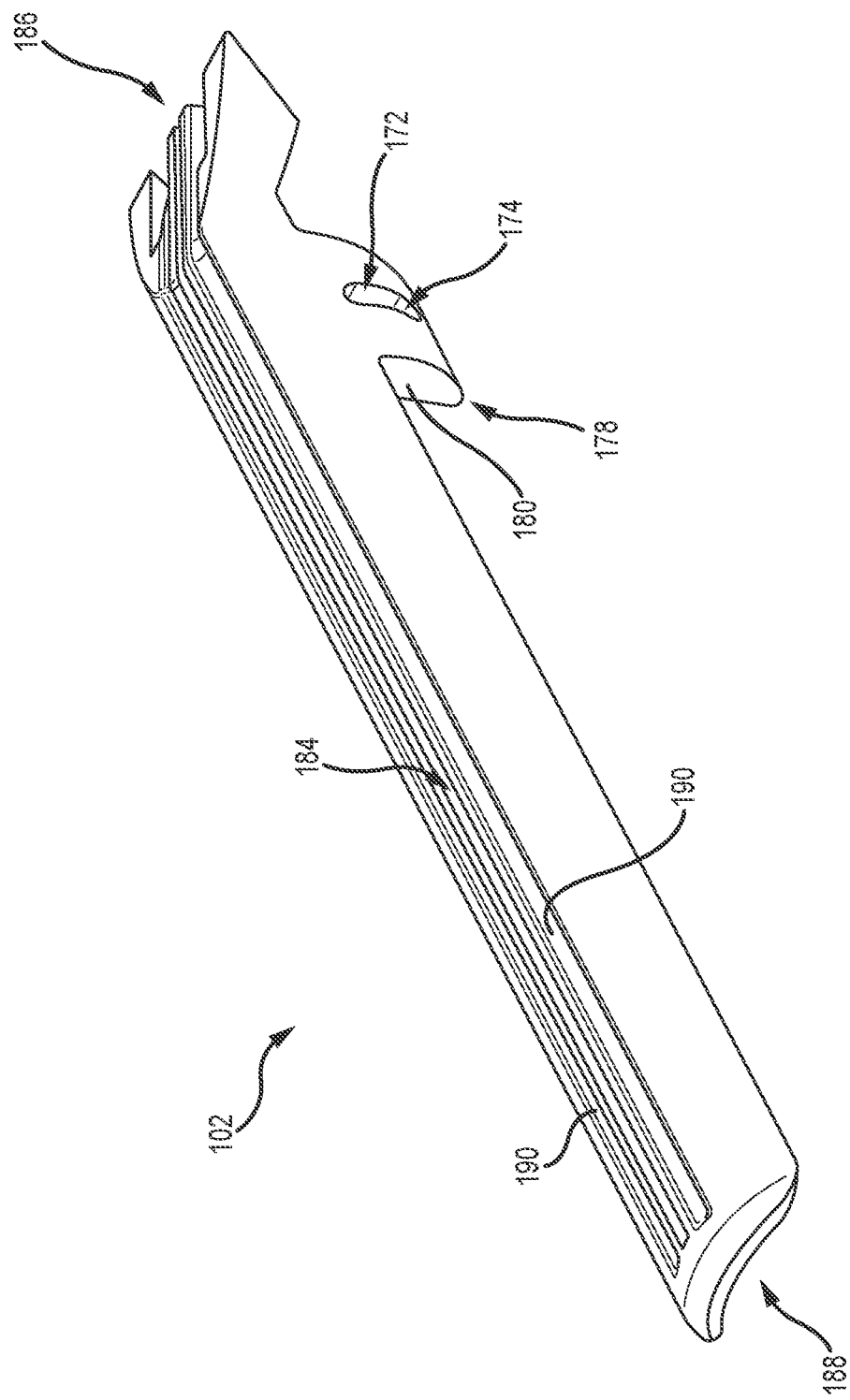
FIG. 8 is a perspective view of an anvil in the stapler in FIG. 1B.

Continuing with FIG. 8, in some embodiments, the anvil 102 or linkage mechanism 172 may include a tissue stop mechanism 178. The tissue stop mechanism 178 may be a feature in the anvil 102 and/or the support jaw 103 (or cartridge 106 or housing 104) configured to prevent tissue from being positioned beyond the stapling region between the anvil 102 and the support jaw 103. That is, the tissue stop mechanism 178 is configured to prevent the stapler 100 from cutting tissue that is not stapled. In some embodiments, the tissue stop mechanism 178 includes a surface 180 in the anvil 102 that is selected and shaped so as to not engage a surface 182 in the cartridge 106 (see e.g. FIGS. 14-15) and damage tissue clamped between the support jaw 103 and the anvil 102 when the anvil is moved from the open position to the clamped position.

The anvil 102 may also have a slot 184 shaped and configured to receive or guide a cutting mechanism 108 or a member 118, 120 of a cutting mechanism 108 as the cutting mechanism 108 travels distally to cut tissue clamped between the support jaw 103 and the anvil 102. The slot 184 may extend from the proximal region 186 of the anvil 102 to a position short of the distal end 188 of the anvil 102. The slot 184 may be shaped to limit the cutting mechanism 108 or member 118, 120 thereof to translation and/or prevent the cutting mechanism 108 or member 118, 120 from extending beyond the distal end 188 of the anvil 102.

Figure 20A:
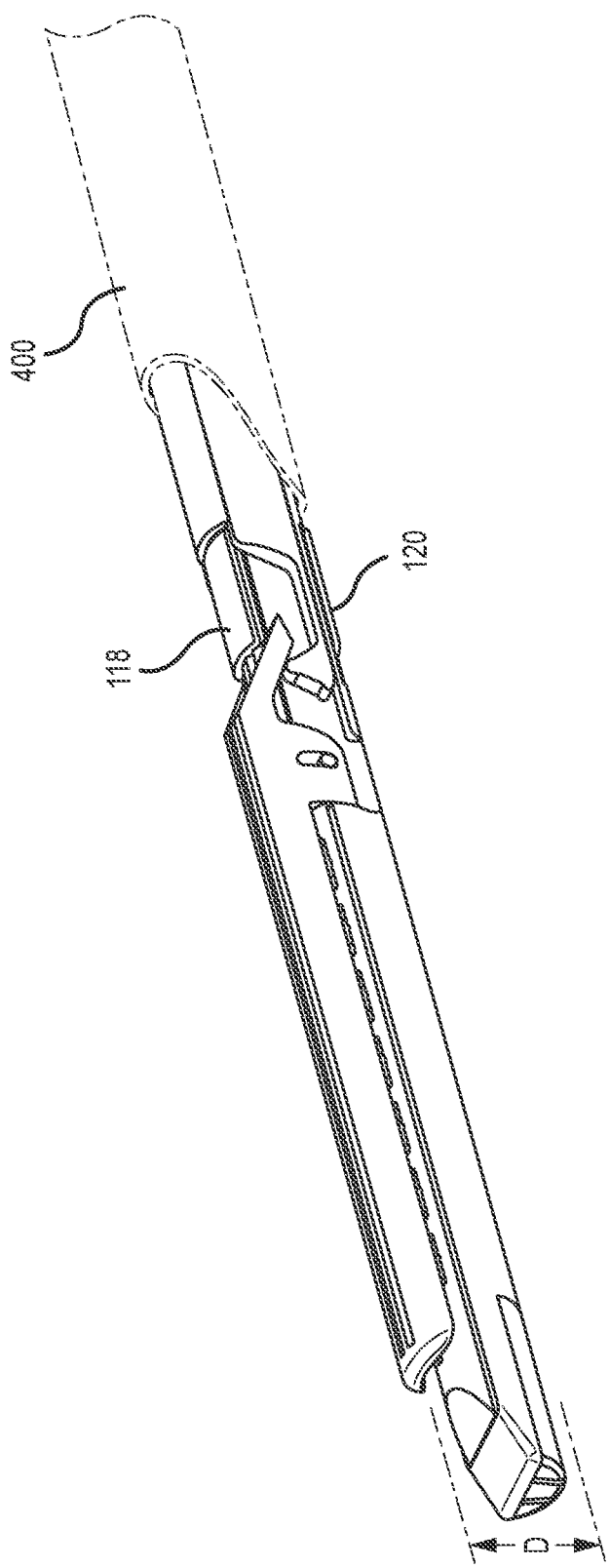
FIG. 20A is a perspective view of the stapler in FIG. 1B.

In some embodiments, the anvil 102 has one or more guides 190 (see e.g. FIG. 9), configured to guide the cutting mechanism 108 or member 118, 120 of the cutting mechanism 108 as the cutting mechanism 108 travels down the anvil 102 (see e.g. FIGS. 20A-20C). The guides 190 in the anvil 102 may correspond to or engage guides 192 in the cutting mechanism 108. In some embodiments, the guide(s) 190 in the anvil 102 may be one or more recesses 190 that engage corresponding one or more ridges or protrusions 192 in the upper member 118 of the cutting mechanism 108, as illustrated.

In some embodiments, guides 192 in the cutting mechanism 108 may be protrusions that do not extend an entire length of the cutting mechanism 108 or member 118, 120, so as to reduce friction between the cutting mechanism 108 or member 118, 120 and the anvil 102.

In some embodiments, the guide(s) 192 in the cutting mechanism 108 may be recesses (not illustrated). In some embodiments, the guide(s) 190 in the anvil 102 may be protrusions (not illustrated) in the anvil 102. In some embodiments the anvil 102 may have a first guide 190 that is a recess or groove, and a second guide 190 that is a protrusion or flange (not illustrated). Those skilled in the art will readily envision any number of means of providing a first and/or second guide 190 to guide the cutting mechanism 108 as it travels towards the distal region of the stapler 100, all of which means are contemplated herein.

In some embodiments, the anvil 102 is sized so as to fit through a cannula 400 having a nominal inner diameter of 8.0 mm. In some embodiments, the anvil 102 is sized so as to fit through a cannula 400 having an inner diameter of 8.6 mm or less. In some embodiments, the anvil 102 is sized so as to fit through a cannula 400 having a nominal inner diameter of 5.5 mm. In some embodiments, the anvil 102 is sized so as to fit through a cannula 400 having an inner diameter of 5.6 mm or less.

Continuing with FIGS. 9-13, the anvil 102 may have first and/or second cam guides 194, 196. The cam guide(s) 194, 196 may be slots in a portion of the anvil 102 configured to guide one or more cams 128, 130 (see FIG. 2) as the cam(s) 128, 130 move or translate longitudinally into the support jaw 103 or housing 104 to cause motion of the staple pusher(s) 132 and/or the staple(s) 132, 146, 148. The cam guide(s) 194, 196 may assist in maintaining the cam(s) 128, 130 positioned at an angle θ relative to each other; for example, the second and/or third slots 142, 144 in the cartridge 106 and the cam guide(s) 194, 196 may guide the translating cam(s) 128, 130 at an oblique angle θ relative to each other, so as to effectuate motion of the staple pushers 132, 146, 148 at the oblique angle θ relative to each other (see also FIG. 5 illustrated the cartridge 106). Put another way, the cam guides 1974, 196 may effectuate a first travel path on a first staple pusher 146 and a second travel path on a second staple pusher 148, the first travel path being at an oblique angle θ relative to the second travel path.

Figure 11:
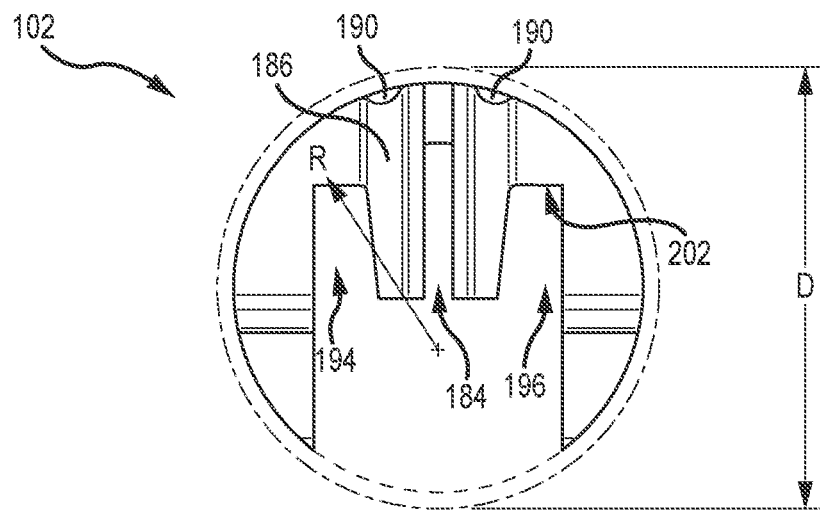
FIG. 11 is a back view of the anvil in FIG. 8.
Figure 12:
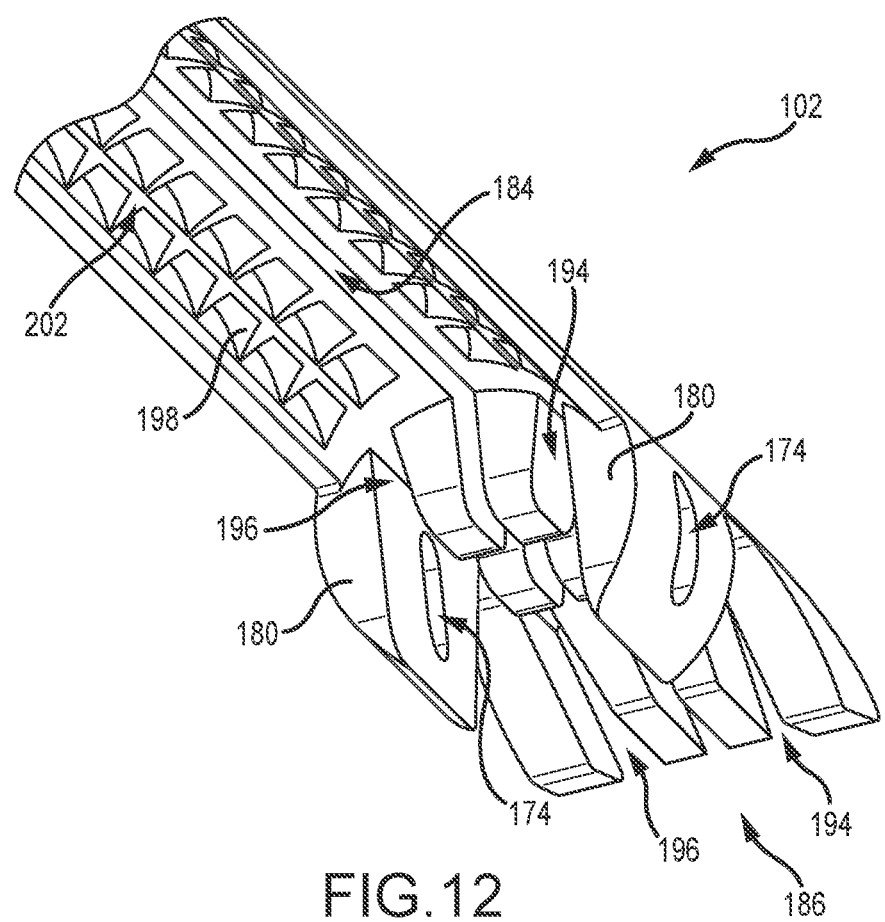
FIG. 12 is a perspective view of features in the anvil in FIG. 8.
Figure 13:
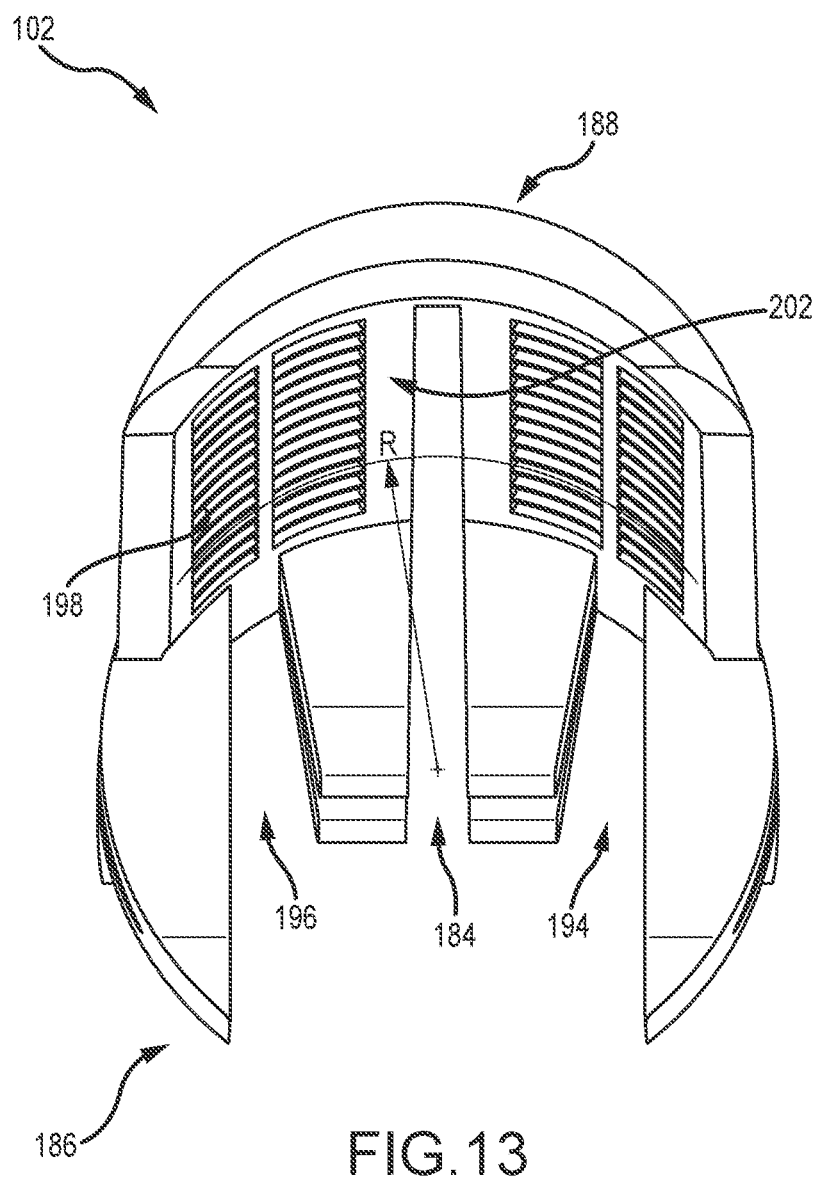
FIG. 13 is a perspective view of features in the anvil in FIG. 8.

With brief reference to FIGS. 11 and 13, the anvil 102 may have a curved tissue clamping interface 202, and the cartridge 106 may have a curved tissue clamping interface 204 (see e.g. FIG. 3) configured to oppose the curved tissue clamping interface 202 of the anvil 102 when the stapler 100 is in a clamped or closed configuration (see e.g. FIGS. 15 and 17). That is, in some embodiments, the anvil 102 may be curved to provide a curved beam in flexure and utilize the compression strength of the material to react against the staple forming forces from the opposing sides. More specifically, the curved beam may prevent the anvil 102 from undesired deformation; in turn, the curved beam may assist in proper staple formation. Those skilled in the art will understand that the term "curved tissue clamping interface" is intended to reference a generally curved clamping surface that may or may not be interrupted by one or more recesses, protrusions, and/or flat regions.

Together, the curved tissue clamping interfaces 202, 204 may be configured to clamp tissue therebetween when the anvil 102 is in the clamped position (illustrated in FIG. 17). The curved tissue clamping interfaces 202, 204 may be configured to abut or nest together when the anvil 102 is in the closed position (illustrated in FIG. 15). In some embodiments, a portion of one or both of the curved tissue clamping interfaces 202, 204 may have a radius of curvature R that is between 40% and 60% of the envelope diameter. For example, for an envelope diameter of 5.6 mm, the radius of curvature R may be between 2.24 mm and 3.36 mm. In some embodiments, the envelope diameter D may be about 5.6 mm, and the radius of curvature R may be between about 2.6 mm and about 2.8 mm. In some embodiments, the radius of curvature may be about 48% of the envelope diameter D, or about 2.69 mm where the envelope diameter D is 5.6 mm.

A portion of the curved tissue clamping interface 204 in the cartridge 106 may have a corresponding or similarly constrained radius of curvature, so as to nest with or clamp tissue with the anvil 102. In some embodiments, a portion of one or both of the curved tissue clamping interfaces 202, 204 has a radius of curvature between 45% and 55% of the envelope diameter. In some embodiments, the radius of curvature is between 47% and 52% of the envelope diameter.

The curved tissue clamping interfaces 202,204 may be configured to provide a cuff that is larger than a cuff normally achieved with staplers having similar nominal sizes (e.g. envelope diameters). Those skilled in the art will understand that a cuff in stapled and transected tissue is defined as the distance from the edge of the transected tissue to the first inside staple row. Cuff width is important because a greater cuff reduces the likelihood that the tissue will pull through the staples, or that the staples will tear out. In some embodiments, the cuff width W is greater than 0.5 mm. In some embodiments, the cuff width W is greater than 0.6 mm. In some embodiments, the cuff width W is about 0.7 mm, or greater. In some embodiments, the cuff width W is 0.8 mm or greater. In some embodiments, the cuff width W is 0.9 mm or greater. In some embodiments, the cuff width W is about 1.6 mm. In some embodiments, the cuff width W is greater than 0.5 mm up to about 1.6 mm. In some embodiments, the envelope diameter D is 5.6 mm or less, and the cuff width W is greater than 0.5 mm. In some embodiments, the envelope diameter D is 5.6 mm or less, and the cuff width W is about 0.7 mm. In some embodiments, the cuff width W is a function of the angle θ, a radius of curvature of the curved tissue clamping interfaces 202, 204, and the size of the staples 150. The staples 150 and angle θ may be configured based on currently known standard leg sizes, or as yet to be developed standard sizes, such as, for example, 2.0 mm, 2.5 mm, 3.0 mm, 3.5 mm, 3.8 mm, 4.1 mm, 4.8 mm, or others.

Returning now to FIG. 12, the anvil 102 may have one or more forming pockets 198 configured to form and/or fold the staples(s) 150, 152, 154, 156 as the staple(s) 150, 152, 154, 156 are pushed out of the cartridge 106 and through tissue, into the anvil 102. The forming pocket(s) 198 may be configured substantially in a manner as is known in the art. However, the forming pockets 198 may be angled or positioned in a manner suitable for properly forming the staple(s) 150, 152, 154, 156 in embodiments in which the staple(s) 150, 52, 154, 156 and staple pushers 132, 146, 148 translate at an angle θ relative to each other, or embodiments in which the anvil 102 and cartridge 106 have curved tissue clamping interfaces 202, 204. The forming pockets 198 may interrupt engagement of tissue by the curved tissue clamping interface 202.

Figure 14:
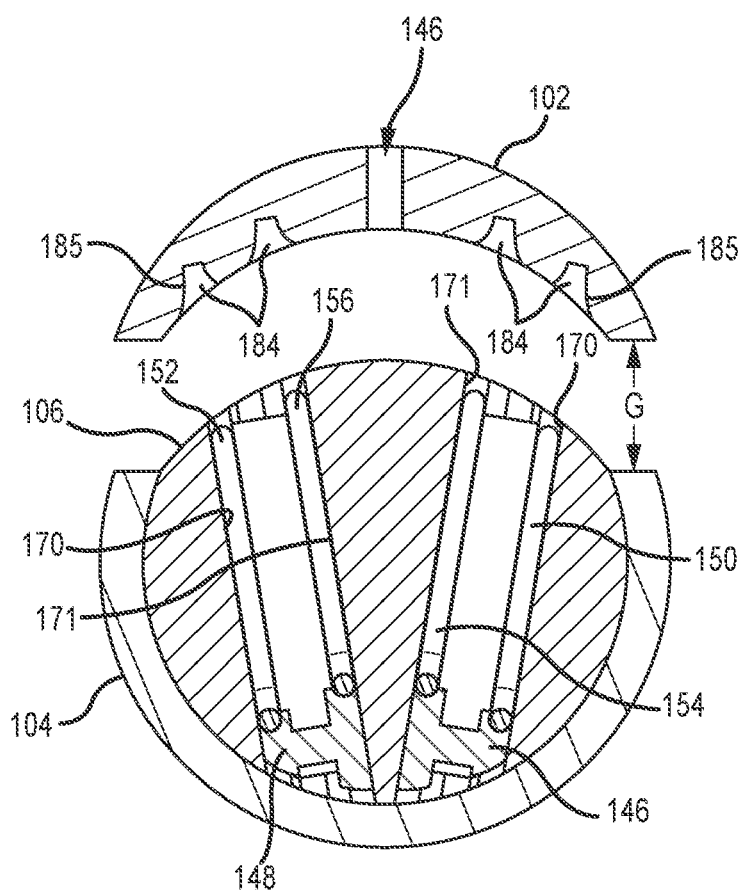
FIG. 14 is a cross-section view of a cartridge and anvil suitable for the stapler in FIG. 1B.

Turning now to FIG. 14, in some embodiments, the stapler 100 may provide for a substantially consistent fixed maximum device gap G across a transverse cross-section of tissue and/or a longitudinal cross-section of tissue during staple firing and/or tissue clamping. In some embodiments, the forming pockets 184 in the anvil 102 are shaped and positioned so as to assist in guiding or driving staples 150, 152, 154, 156 in a direction normal to tissue clamped between the anvil 102 and cartridge 106 or support jaw 103. In some embodiments, the stapler 100 has an envelope diameter D of 5.6 mm or less in a closed configuration, and is configured to allow a maximum device gap G of greater than 1.5 mm, and up to 2.0 mm between the curved tissue clamping interfaces 202, 204. In some embodiments, the stapler 100 has an envelope diameter of 8.6 mm or less in a closed configuration, and is configured to allow a maximum device gap G of 2.0 mm or more.

In some embodiments, the stapler 100 is configured fit through a cannula 400 having an inner diameter 402 of 5.6 mm or less in a closed configuration, and to place staples having a nominal leg length L of 3.5 mm in a patient while allowing a maximum device gap G of more than 1.5 mm between the curved tissue clamping interfaces 202, 204. In some embodiments, the stapler 100 is configured to fit through a cannula 400 having an inner diameter 402 of 8.6 mm or less in a closed configuration, and to place staples having a nominal leg length L of 4.8 mm in a patient and allow a maximum device gap G of at least 2.0 mm between the curved tissue clamping interfaces 202, 204.

In some embodiments, an angle θ between a first set of staples 150, 154 and a second set of staples 152, 156, provides a relatively wide cuff, as previously described herein. The wider cuff achieved using a stapler 100 configured for a 5.5 mm cannula 400 may be comparable to a cuff achieved using a standard stapler configured for a 12 mm diameter cannula 400, and may be about 0.7 mm or more. In some embodiments, a curved cartridge 106 and rotated or angled staple(s) create additional space between the knife/cutting mechanism and the inner row of staples, increasing the width of the tissue "cuff" that is created following staple formation and tissue transection.

Continuing with FIG. 14, lead-in features 185 of the forming pockets 184 may match the rotation angle θ of the staples within the cartridge 106. See also FIG. 10. That is, the lead-in features 185 may be between about 4 degrees and about 30 degrees from each other, or less than or up to about 90 degrees from each other in some embodiments. The lead-in features 185 may include any lead-in means, including bevels, chamfers, reliefs, or any other features known in the art and configured to assist in guiding staples into the forming pockets 184.

Turning now to FIGS. 15-17, as previously described, the anvil 102 may be movable relative to the support jaw 103 between a closed position as illustrated in FIG. 15, an open position as illustrated in FIG. 16, and a clamped position as illustrated in FIG. 17. In the closed position, the anvil 102 and support jaw 103 may have a compressed envelope dimension or diameter D. That is, the anvil 102 and support jaw 103 together may be configured to pass through a passage having an inner dimension of a particular nominal size. For example, the closed envelope dimension may have a closed envelope diameter D configured to pass through a cannula 400 having an inner dimension or diameter 402 of a particular nominal size, such as 8.6 mm or 5.6 mm in some embodiments.

In some embodiments, the stapler 100 may be tip-biased. That is, the anvil 102 and/or support jaw 103 may be shaped such that a distal end of the stapler 100 will tend to contact first when the stapler 100 is moved towards a closed configuration. A tip-biased stapler 100 may be configured such that a slight flexure of the anvil 102 and/or support jaw 103 allows full compression to a closed configuration wherein the anvil 102 and cartridge 106 make contact along a substantial or majority portion of the clamping interfaces 202, 204.

After passing through or partially through the cannula 400, the anvil 102 may be actuated to move into an open position, such as the open position illustrated in FIG. 16. In the open position, the anvil 102 may be rotated, rotated and translated, or moved such that a distal portion 188 of the anvil 102 is positioned further away from the support jaw 103 than is the proximal portion 186. With the stapler 100 in the open configuration, a surgeon may place tissue between the support jaw 103 and the anvil 102 in preparation for surgical cutting and/or stapling of tissue.

As illustrated in FIG. 17, the anvil 102 may be movable to a clamped position. The clamped position may be selected or designed so as to achieve a substantially consistent maximum device gap G (see e.g. FIGS. 10, 14) between the anvil 102 and the cartridge 106 or support jaw 103, or between the clamping interfaces 202, 204 thereof, during firing and as previously described herein. In some embodiments, the clamped position may be selected or designed such that the anvil 102 and support jaw 103 have an envelope dimension or diameter D2 that is greater than the compressed envelope dimension or diameter D in the closed configuration. In some embodiments, the clamped configuration results in an envelope dimension or diameter D that is greater than the inner diameter 402 or dimension of the cannula 400 through which the stapler 100 has been passed.

In some embodiments, an upper anvil positioner 110 and a lower anvil positioner 112 may be provided and configured to effectuate motion of the anvil 102 relative to the support jaw 103. That is, the upper anvil positioner 110 and/or the lower anvil positioner 112 may be configured to manipulate or move a pivot point of the anvil 102 as the anvil 102 is moved between the closed, open, and/or clamped positions.

Figure 18:
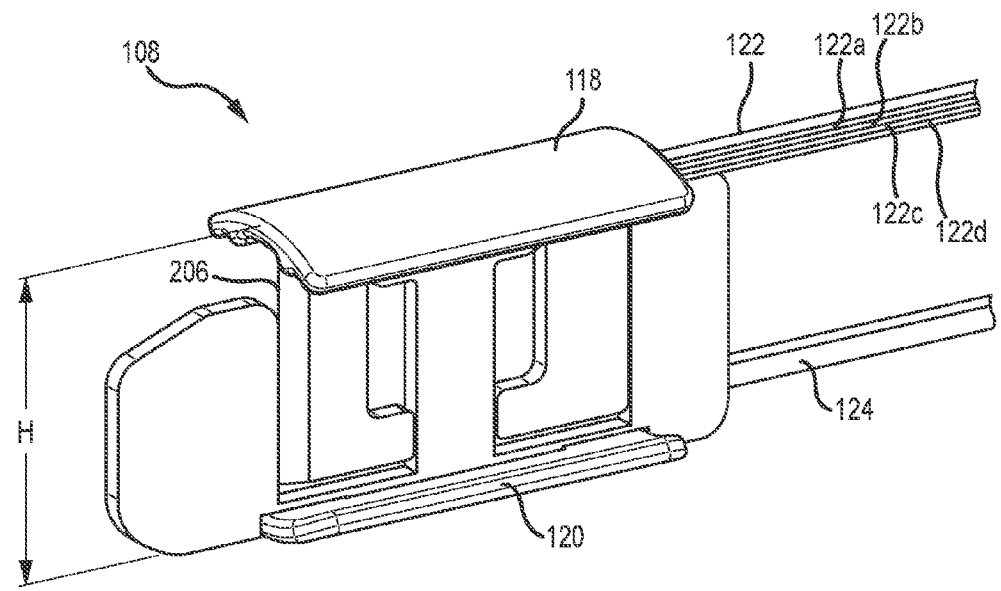
FIG. 18 is a perspective view of a cutting mechanism in the stapler in FIG. 1B.
Figure 19:
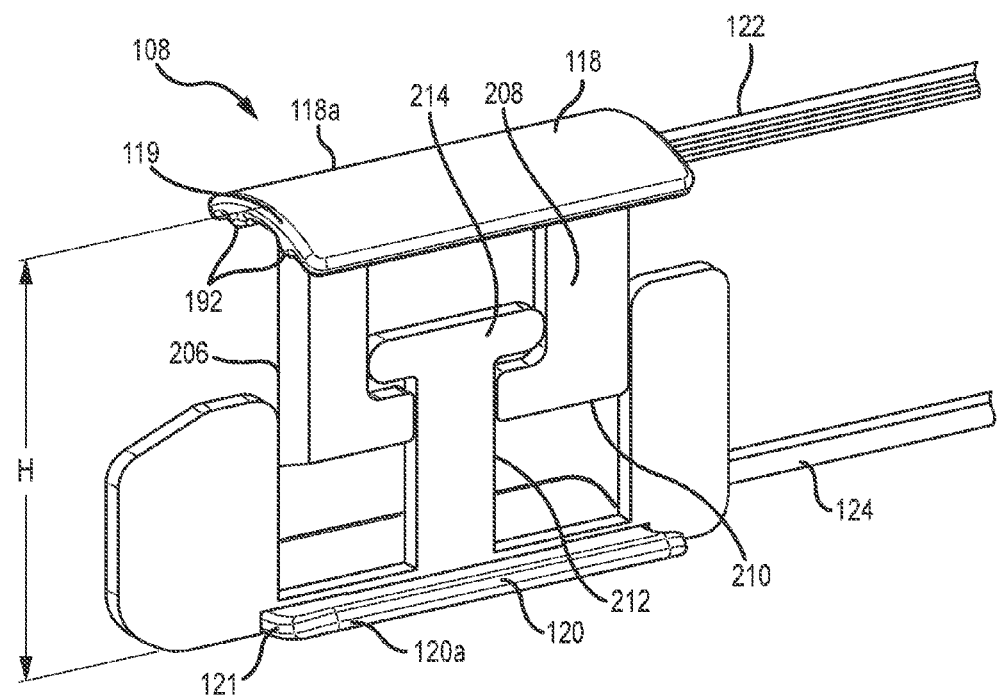
FIG. 19 is a perspective view of a cutting mechanism in the stapler in FIG. 1B.

Turning now to FIGS. 18-20C, and as previously described, the stapler 100 may have an expandable cutting mechanism 108 and/or clamping member configured to move between a collapsed configuration and an expanded configuration. FIG. 18 illustrates the cutting mechanism 108 in a collapsed configuration, and FIG. 19 illustrates the cutting mechanism in an expanded configuration.

In the collapsed configuration (e.g. FIG. 18), the cutting mechanism 108 may have a height H or envelope diameter that is less than a combined height of the anvil 102 and the support jaw 103 (or the rest of the stapler 100 generally) or less than the envelope diameter D. In the expanded configuration (e.g. FIG. 19), the cutting mechanism 108 may have or may approach a height H that is greater than a combined height of the anvil 102 and the support jaw 103 when the anvil 102 is in the clamped configuration. Put another way, the height H of the cutting mechanism 108 in the collapsed configuration may be less than the envelope diameter D of the stapler 100 when the stapler 100 is in the closed and/or clamped configurations. In some embodiments, the height H of the cutting mechanism 108 in the collapsed configuration may be less than the combined envelope diameter of the anvil 102 and the support jaw 103 when the stapler 100 or anvil 102 is in the closed and/or clamped configurations or positions. In some embodiments, the height H of the cutting mechanism 108 in the expanded configuration may be greater than the combined envelope diameter D of the anvil 102 and the support jaw 103 when the stapler 100 or anvil 102 is in the closed and/or clamped configuration or position. The height H of the cutting mechanism 108 in the collapsed configuration may be less than the inner diameter 402 of the cannula 400. The height H of the cutting mechanism 108 in the expanded configuration may be greater than the inner diameter 402 of the cannula 400.

The expandable cutting mechanism 108 may have a first member 118 and a second member 120 that are expandable, translatable, or movable relative to each other. In some embodiments, a first one of the members 118, 120 is movable both longitudinally and transversely relative to the support jaw 103 or cartridge 106, and a second one of the members 118, 120 is limited to longitudinal movement relative to the support jaw 103 or cartridge 106. In some embodiments, both of the members 118, 120 are movable both longitudinally and transversely relative to the support jaw 103 or cartridge 106. In some embodiments, a first one of the members 118, 120 is rotatable relative to a second one of the members 118, 120. That is, for example, a first member 118, 120 may rotate slightly as the cutting member 108 expands to move up the anvil 102 and support jaw 103. The slight rotation may be limited by flanges and/or legs in the members 118, 120.

One of the members 118, 120 may have a knife edge or cutting portion 206, and may be configured to travel through or partially through a slot 140 in the cartridge 106 and/or a slot 184 in the anvil 102 so as to cut tissue clamped between the anvil 102 and the support jaw 103. The other one of the members 118, 120 may be configured to travel with the first member 118, 120, such that, together, the first and second members 118, 120 may provide a strengthening effect on the stapler 100. More specifically, and as illustrated in FIG. 20C, the cutting mechanism 108 may be configured to apply a supportive clamping force on tissue clamped between the anvil 102 and the support jaw 103 when the cutting mechanism 108 is in a distal position and/or moving distally, and expanded about the anvil 102 and support jaw 103.

In some embodiments, the upper anvil positioner 110 is configured to rotate relative to the support jaw 103 and assist in guiding the cutting mechanism 108.

In some embodiments, the expandable cutting mechanism 108 is coupled to or comprises a first actuator 122 coupled to one of the members 118, 120, such as the first member 118, and a second actuator coupled to the other one of the members 118, 129, such as the second member 120. In some embodiments one or both of the actuators 122, 124 is flexible. In some embodiments, a first actuator 122 is configured to apply a retracting force when actuated (e.g. pull the cutting mechanism 108 towards the user or proximal region of the stapler 100), and a second actuator 124 is configured to apply an extending force when actuated (e.g. push the cutting mechanism 108 away from the user or towards the distal region of the stapler 100). In some embodiments, a flexible actuator 122, 124 may be configured with a suitable rigidity for maintaining the member 118, 120 to which the actuator 122, 124 is coupled oriented relative to the other member 118, 120. Put another way, an actuator 122, 124, such as the first actuator 122 may provide a limited pushing or extending force on the cutting mechanism 108, and a greater retracting force when retraction is required.

In some embodiments, the cutting mechanism 108 is configured to move between a collapsed configuration wherein the cutting portion 206 is not in line with a tissue cutting region defined by the anvil 102 and the support jaw 103 and an expanded configuration wherein the cutting portion 206 is in line with the tissue cutting region, the tissue cutting region defined by a device gap G between the anvil 102 and the support jaw 103 (see e.g. FIGS. 19 and 20A-20C).

One or both of the actuators 122, 124, (as illustrated, the first actuator 122) may be configured so as to be flexible enough to allow the expandable cutting mechanism 108 to expand (e.g. the first member 118 may move upward and/or the second member 120 may move downward) as the expandable cutting mechanism 108 travels distally, and rigid enough to apply a strong enough force to cause the member 118, 120 to which the actuator 122, 124 is attached to move distally, or at least remain oriented relative to the other member. That is, in some embodiments the first actuator 122 may orient the first member 118 relative to the second member 120 while the second actuator 124 primarily causes the cutting mechanism 108 to move distally.

It should be understood that the first and second actuators 122, 124 may be coupled to the first and second members 118, 120 using any means known in the art and suitable for ensuring reliable control of the first and second members 118, 120. In some embodiments, one or both actuator(s) 122, 124 has a number of layers that are fused together, or may comprise a laminated beam. For example, a plurality of layers 122a, 122b, 122c, 122d comprising a high strength steel may be provided, and coupled to each other using a binding agent to achieve a suitable flexibility in the actuator 122, 124 and extending force on the member 118, 120. In some embodiments, neither actuator 122, 124 has a laminated beam, but may comprise a material selected for a suitable flexibility and strength for positioning the cutting mechanism 108 or member 118, 120. That is, the actuator(s) 122, 124 should be selected so as to be strong enough to push the cutting mechanism 108 or member(s) 118, 120 distally and flexible enough to move with the cutting mechanism 108 or member(s) 118, 120 as the cutting mechanism 108 expands outside the envelope diameter D.

Continuing with FIGS. 18-19, those skilled in the art will understand that the cutting mechanism 108 may be made of any suitable materials known in the art and suitable for cutting tissue clamped between the anvil 102 and the support jaw 103 or cartridge 106. For example, the first member 118 may be formed of a surgical steel and polished or machined so as to have a sharp cutting portion 206. In some embodiments, the first member 118 has one or more legs 208 with a flange portion(s) 210 that are configured to engage one or more flanges 214 in one or more legs 212 in the second member 120, so as to limit the amount of expansion possible between the first and second members 118, 120. In some embodiments, the legs 208, 212 are configured to allow one member 118, 120 to rotate a given amount relative to the other member 118, 120. In some embodiments, the cartridge 106, slot 140, and/or anvil 102 are configured to maintain a vertical orientation of the cutting mechanism 108.

The cutting mechanism 108 may have a means for limiting expansion between the first and second members 118, 120 to a pre-determined expanded height H, for example, such that, at maximum expansion, the cutting mechanism 108 is configured to assist in preventing the anvil 102 from deforming while clamping tissue. In some embodiments, the cutting mechanism 108 is configured to limit a tissue clamping gap between the anvil 102 and support jaw 103 to a device gap G that is suitable for clamping, cutting, and/or stapling tissue. For example, in some embodiments, the cutting mechanism 108 is configured to squeeze the anvil 102 towards the support jaw 103 a given amount as the cutting mechanism 108 travels from a proximal position towards a distal position. As illustrated most clearly in FIG. 19, in some embodiments, a leading portion 119 of the first member 118 and/or a leading portion 121 of the second member 120 may be positioned on the cutting mechanism 108 at a region that is more distal to the user than is the cutting surface 206. The leading portion(s) 119, 121 may be configured to apply a compressive force on the anvil 102 and support jaw 103 so as to ensure the device gap G is reached prior to a tissue cut, and/or to ensure the maximum device gap G is not exceeded during a tissue cut.

In some embodiments, the cutting mechanism 108 is configured to jam or not travel into a region where the maximum device gap G is not achieved. For example, if the stapler 100 is configured to achieve a maximum device gap G of 2.0 mm, but a portion of the tissue cannot be compressed to 2.0 mm, the cutting mechanism 108 will not travel into regions of tissue that are too thick. In this event, even if the stapler 100 has inadvertently fired staples into the tissue, and those staples are not properly formed, the cutting mechanism 108 will not cut that portion of the tissue that is not properly stapled. The surgeon may then manually retract the cutting mechanism 108, and pry the improperly formed staples out of the tissue.

As illustrated in FIG. 19, those skilled in the art will understand that any part of the first member 118 or the second member 120 may be made unitary, or any part may be a separate component coupled to other components of the cutting mechanism 108. In some embodiments, the legs 208, 212 of the members 118, 120 may be independent features coupled to curved guide portions 118a, 120a of the members 118, 120.

Figure 21:
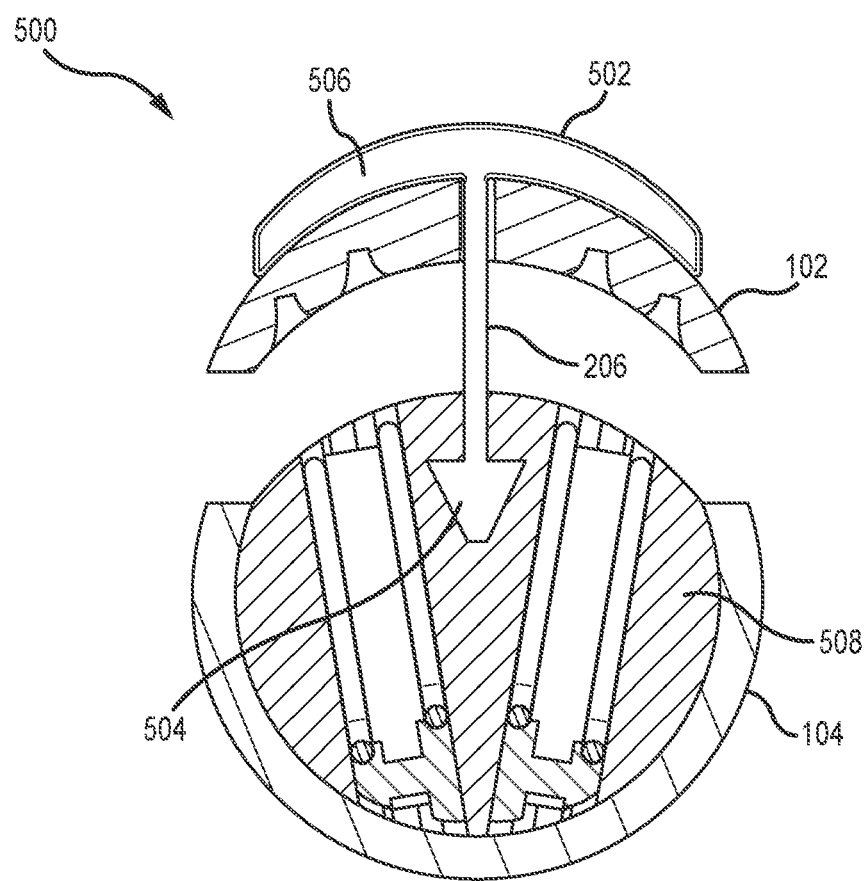
FIG. 21 is a cross-section view of a clamp suitable for a stapler.

With reference now to FIG. 21, in some embodiments, the surgical stapler 500 may have an anchored clamp mechanism 502 with a cutting surface 206 as previously described herein. The anchored clamp mechanism 502 may include a modified I-beam having a first or lower flange 504 and a second or upper flange 506 coupled together such that the modified I-beam does not extend all the way through the diameter of the end effectors, as is the case in currently-available designs. Instead, the I-beam may be anchored at the first flange 504 within the cartridge 508, for example, in the space created by the angle of the staples. In some embodiments, the I-beam may include a first flange 504 shaped to slidingly engage a flange or recess in the cartridge 508. The I-beam may include a surface on one or more of the flanges 504, 506 shaped to slidingly engage an outer surface of the clamp or end effector of the surgical stapler 500.

In some embodiments, the anchored clamp mechanism 502, cutting mechanism 108, or I-beam may be shaped to slide to trail the cam(s) 128, 130 and act as a moving fulcrum in a manner substantially as previously described with reference to the cutting mechanism 108. In some embodiments, the anchored clamp mechanism 502, cutting mechanism 108, or I-beam may be shaped to slide or travel distally As illustrated in FIG. 21, the first flange 504 may allow the anchored clamp mechanism to slide through a recess or channel cutout in the cartridge, while allowing or limiting the maximum device gap G in a manner substantially as previously described with reference to the cutting mechanism 108.

Figure 22:
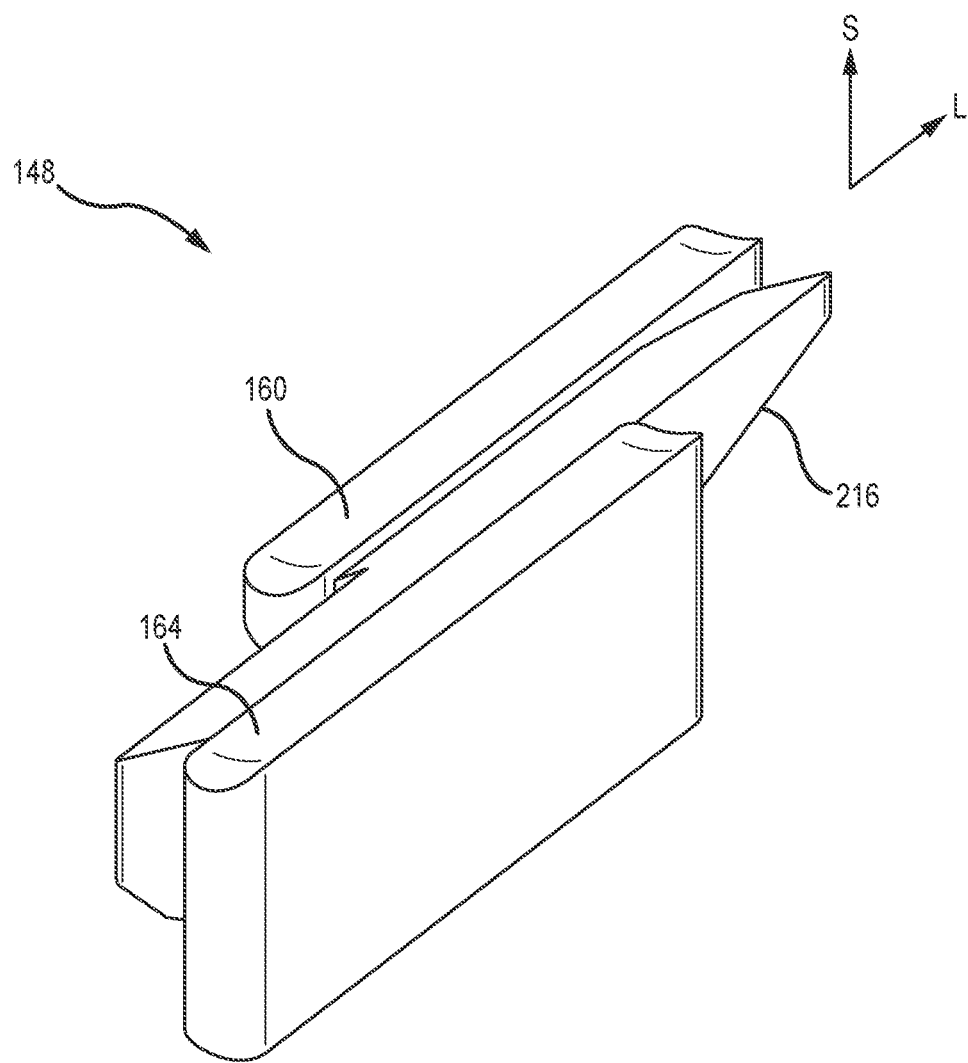
FIG. 22 is a perspective view of a staple pusher in the stapler in FIG. 1B.
Figure 23:
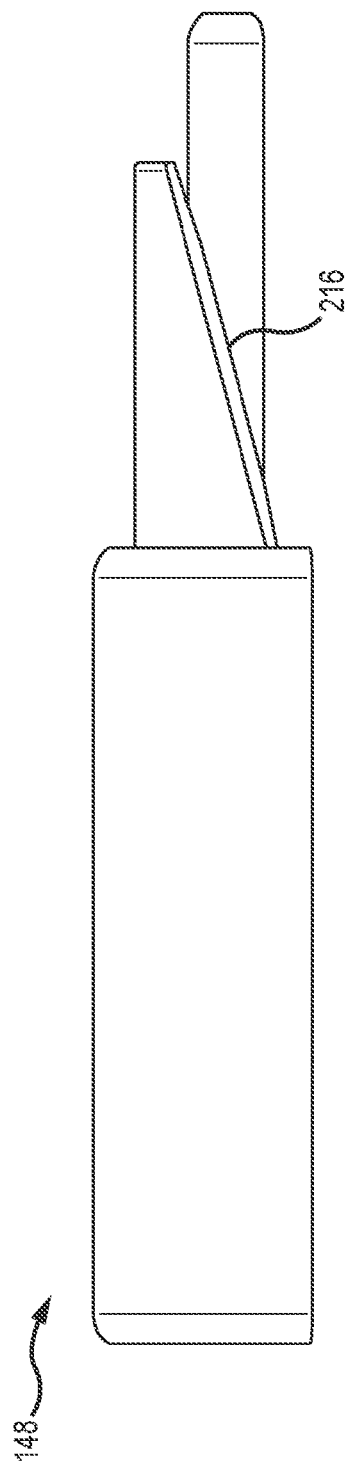
FIG. 23 is a first side view of the staple pusher in FIG. 22.
Figure 24:
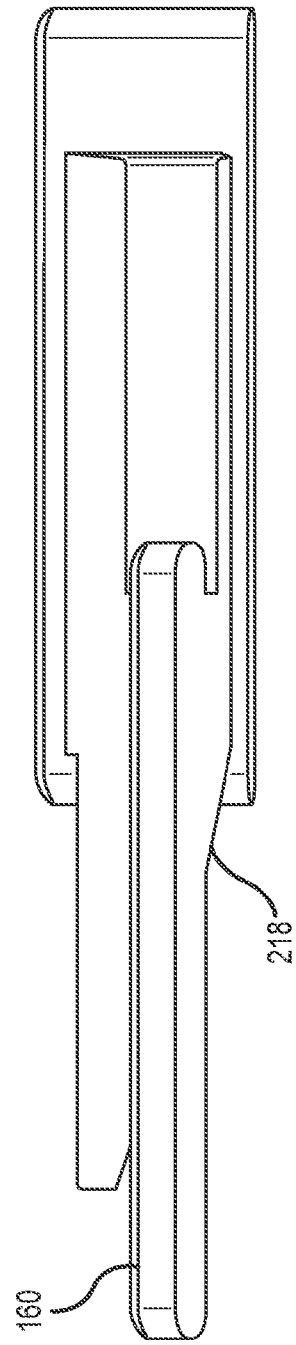
FIG. 24 is a second side view of the staple pusher in FIG. 22.

Turning now to FIGS. 22-24, a staple pusher 148 is illustrated in further detail. The staple pusher 148 may comprise a first cupped region 160 and a second cupped region 164 configured to support two staples substantially as previously described herein. In some embodiments, the cupped regions 160, 164 are configured to support the staples in a staggered but parallel orientation, so as to ensure that the stapled tissue is sealed. As illustrated in FIG. 22, the staple pusher(s) 148 may have a first cammed surface 216 and/or a second cammed surface 218 that is/are configured to, in coordination with a translating cam 128, 130 and the cartridge 106, convert longitudinal motion of the translating cam 128, 130 into a transverse motion, such as at an angle θ oblique relative to another staple pusher 132 to drive staples into tissue clamped between the anvil 102 and the support jaw 103.

Figure 25:
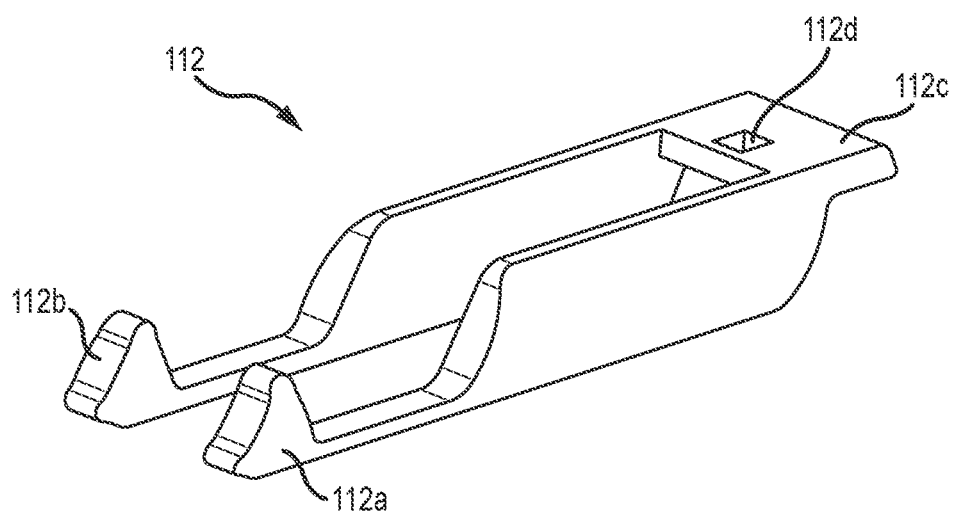
FIG. 25 is a perspective view of a lower anvil positioner in the stapler in FIG. 1B.

FIG. 25 illustrates the lower anvil positioner 112 having, as previously described, flanges 112*a*, 112*b* for assisting in positioning the anvil 102, although those skilled in the art will understand that a single flange 112*a*, 112*b* may be suitable or implemented. In some embodiments, the flanges 112*a* 112*b* are coupled together by way of a bridge 112*c* to enable a single actuator (not illustrated) to effectuate a motion of the lower anvil positioner 112 and/or flange(s) 112*a*, 112*b*. In some embodiments, the lower anvil positioner 112 has a bridge 112*d* for coupling the flanges 112*a*, 112*b*.

Figure 26:
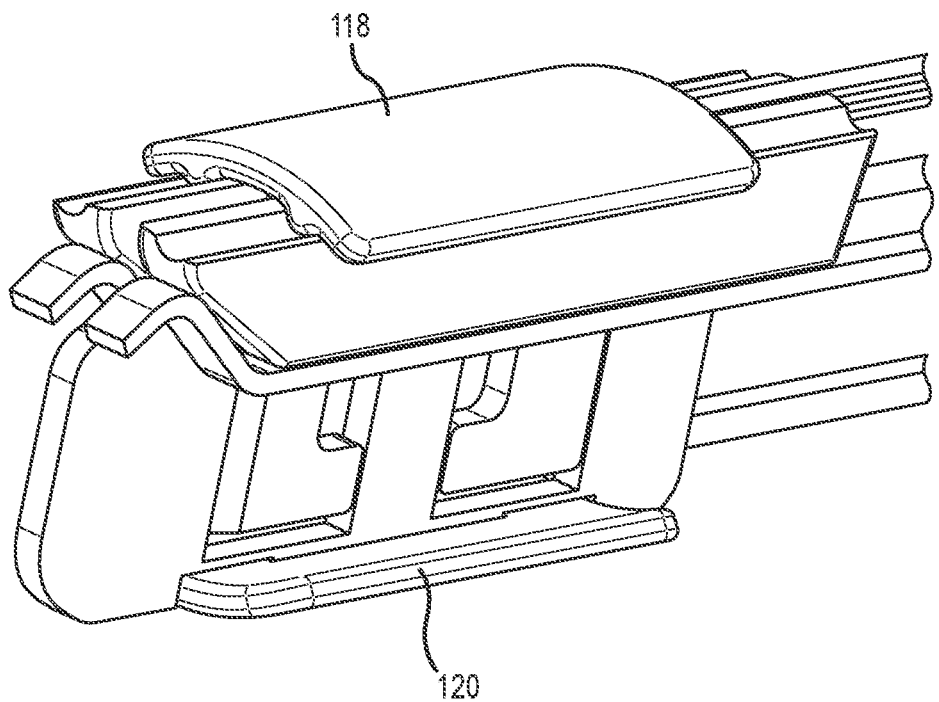
FIG. 26 is a perspective view of some components of the stapler in FIG. 1B.

FIG. 26 illustrates a relationship between the cutting mechanism 108, the spring 113, and the upper anvil positioner 110.

Figure 27:
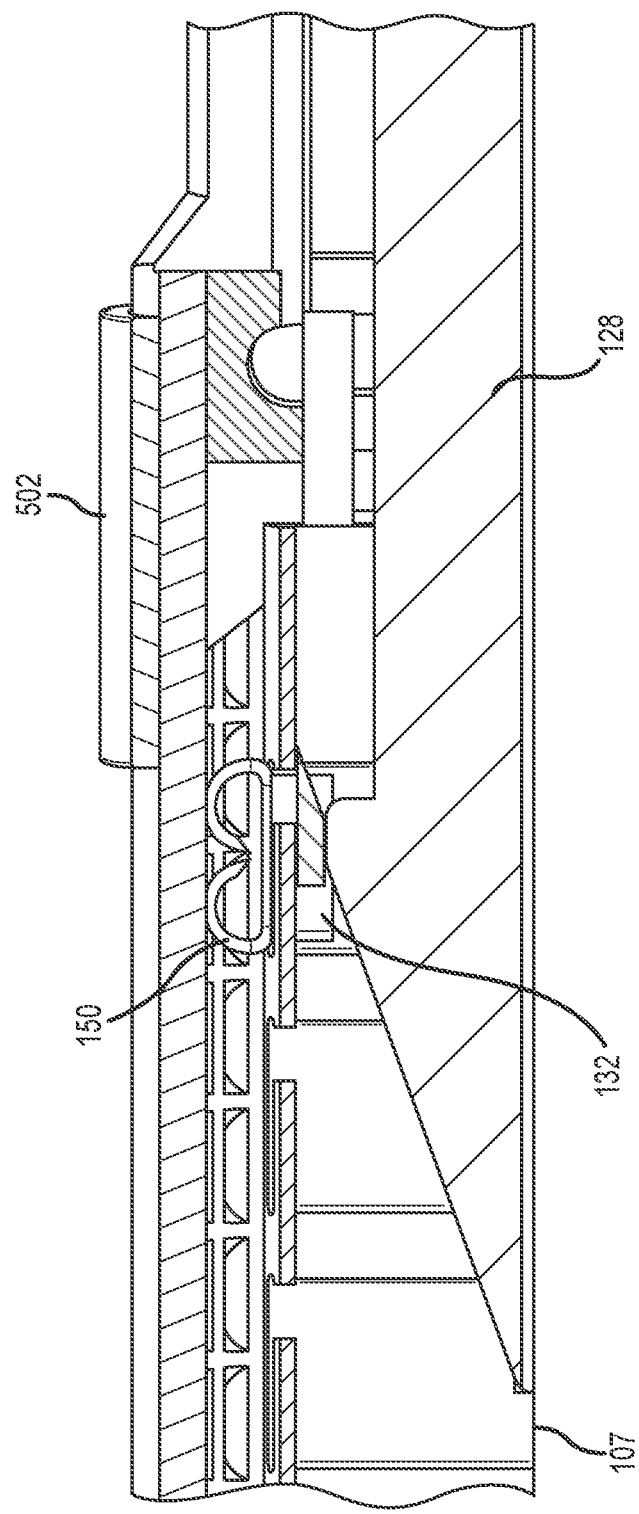
FIG. 27 is a side section view of some components of a stapler.
Figure 28:
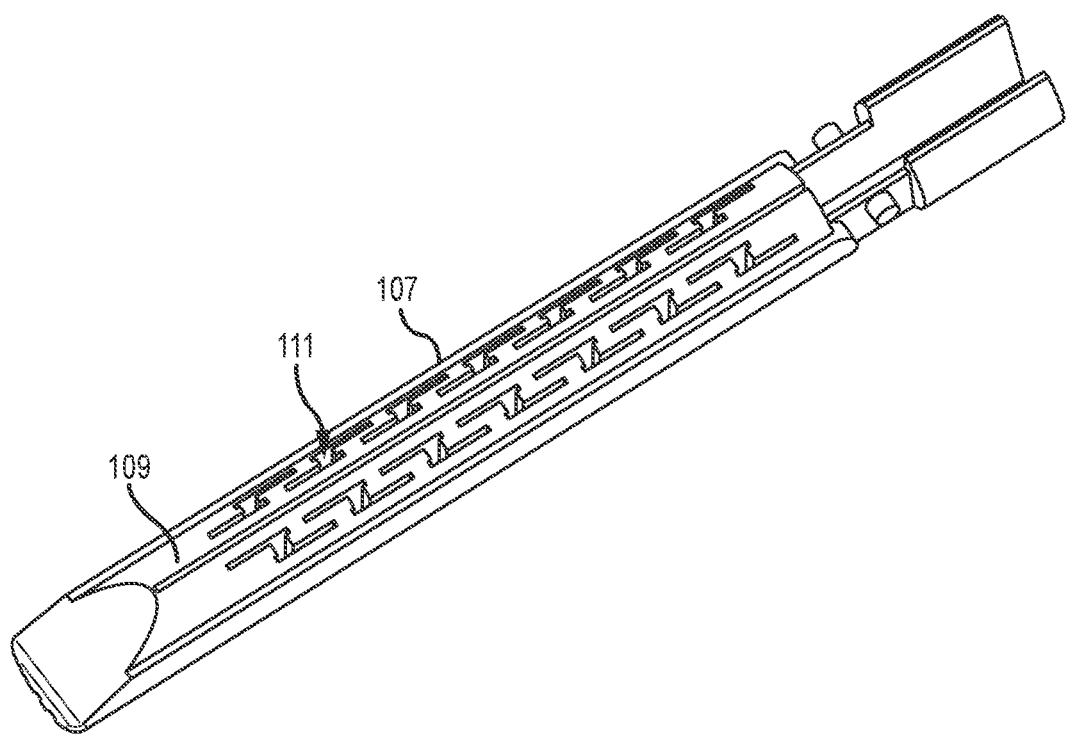
FIG. 28 is a perspective view of an integrated housing.

As illustrated in FIGS. 27-28, in some embodiments, a cartridge housing is not provided. That is, a cartridge 106 and cartridge housing 104 may be integrated in to one piece, an integrated staple housing 107, to form an outer casing. The integrated staple housing 107 may have features to properly guide the staple(s) out of the housing 107 as they are driven by the cam 128, 130 (and staple pusher(s) 132). In embodiments having an integrated staple housing 107, an insert 109, may be coupled to, placed in, or snapped into the center of the integrated housing 107 to complete the medial features of the staple pocket 111. Additionally, the staple pusher(s) 132 may be modified (trimmed) or suitably sized so as to make space to increase a housing wall thickness for strength.

Figure 29:
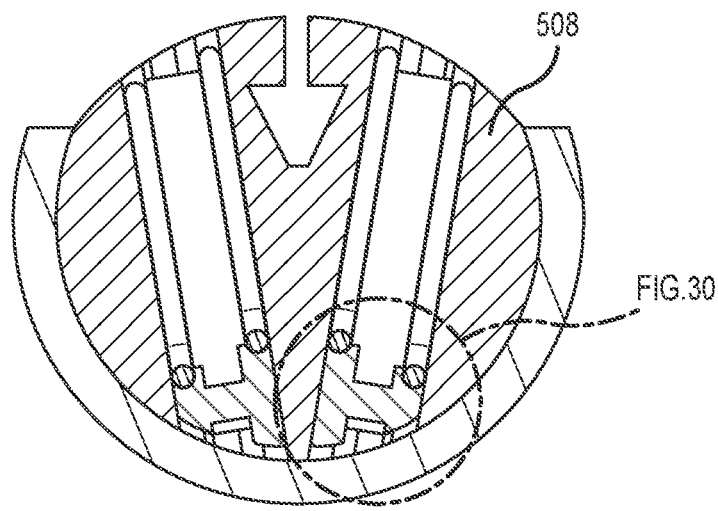
FIG. 29 is a cross-section view of a cartridge, staple pushers, and staples.
Figure 30:
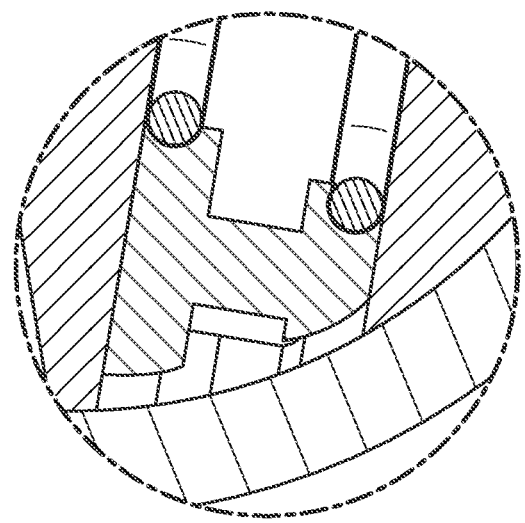
FIG. 30 is a detailed view of the components in FIG. 29.
Figure 31:
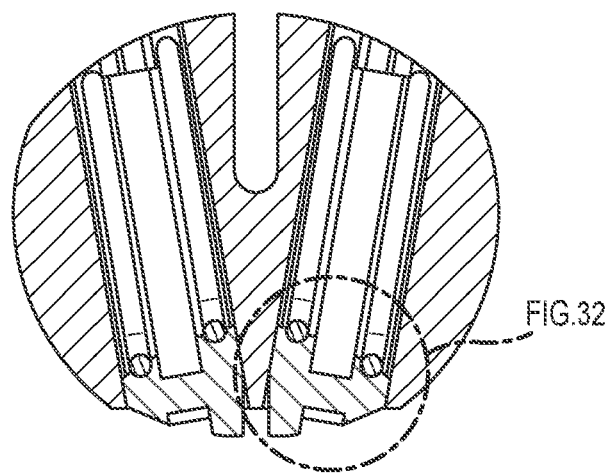
FIG. 31 is a cross-section view of a cartridge, staple pusher, and staples.
Figure 32:
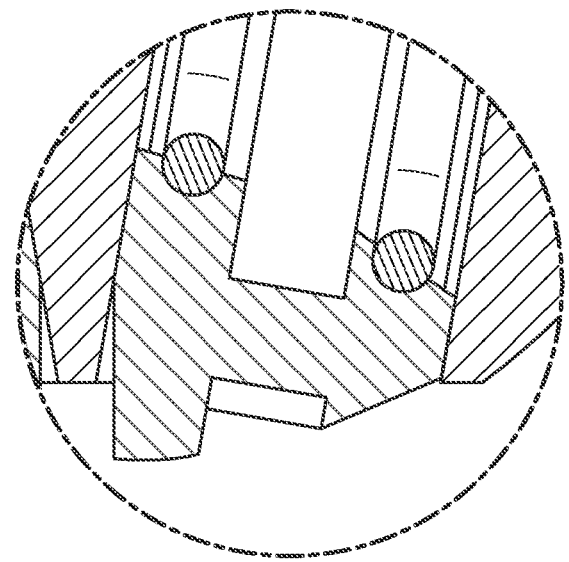
FIG. 32 is a detailed view of the components in FIG. 31.
Figure 33:
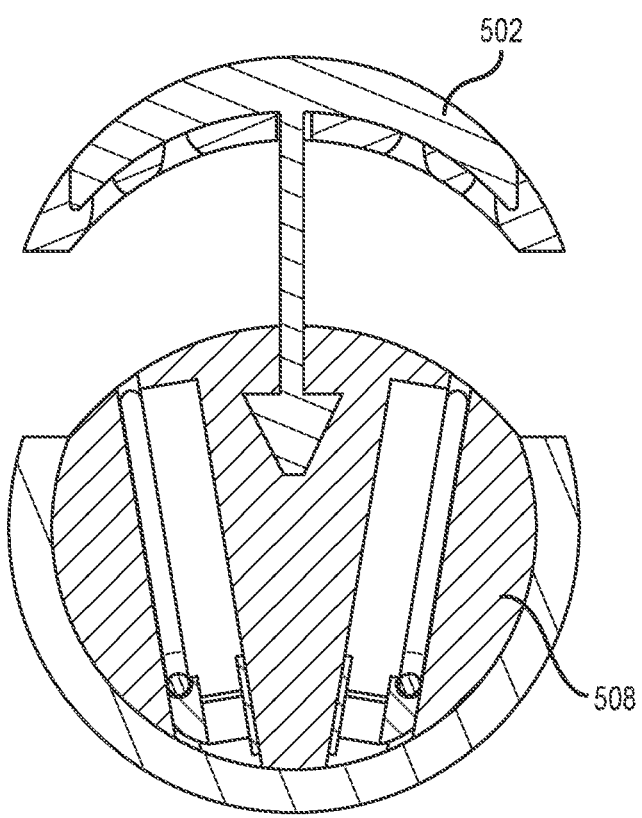
FIG. 33 is a cross-section view of a clamp and other components.
Figure 34:
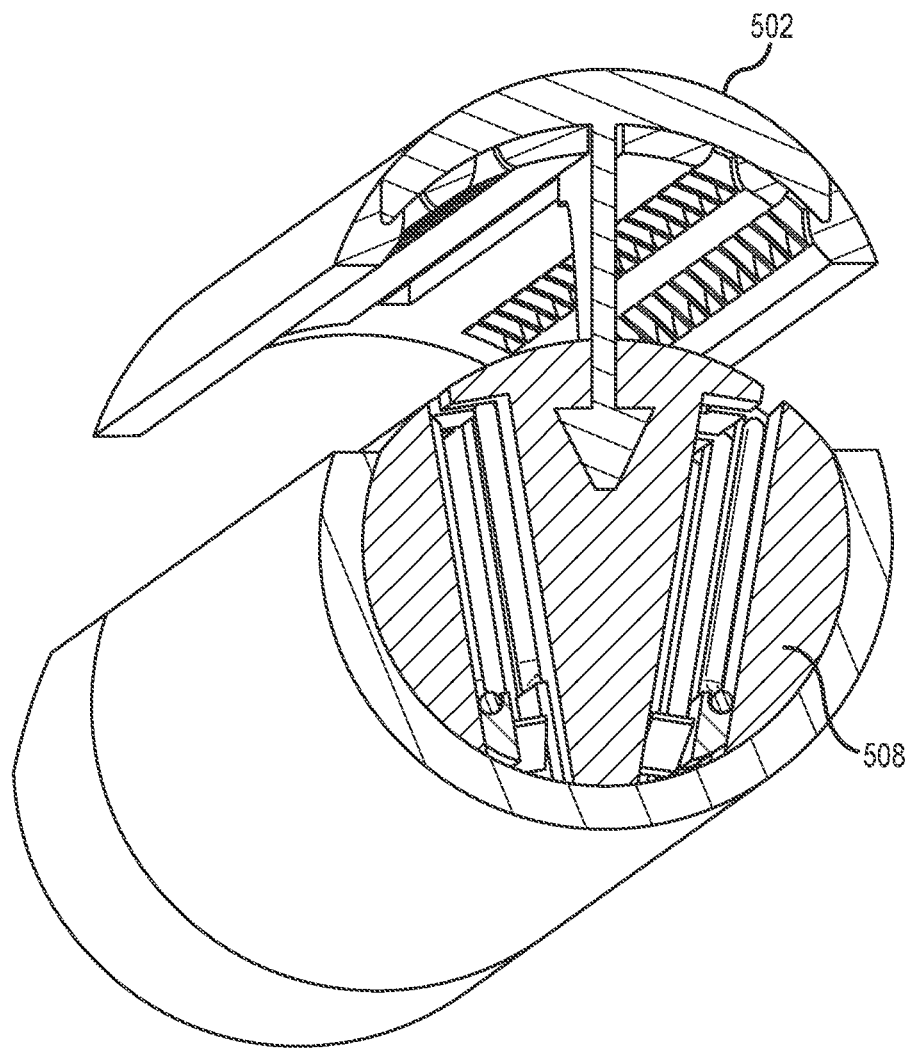
FIG. 34 is a cross-section perspective view of the clamp and other components.
Figure 35A:
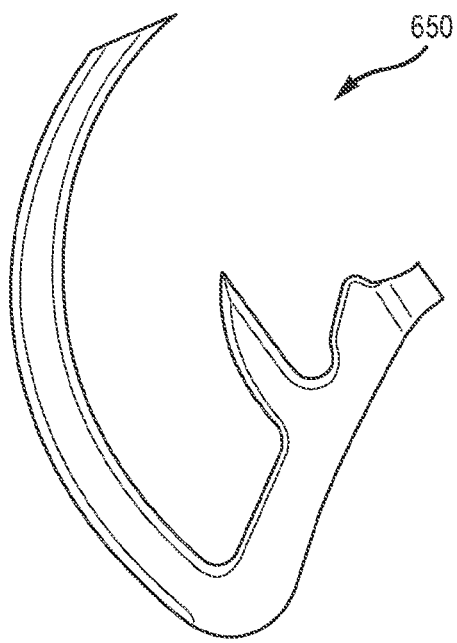
FIG. 35A is a side view of a D-shaped surgical staple prior to placement.
Figure 35B:
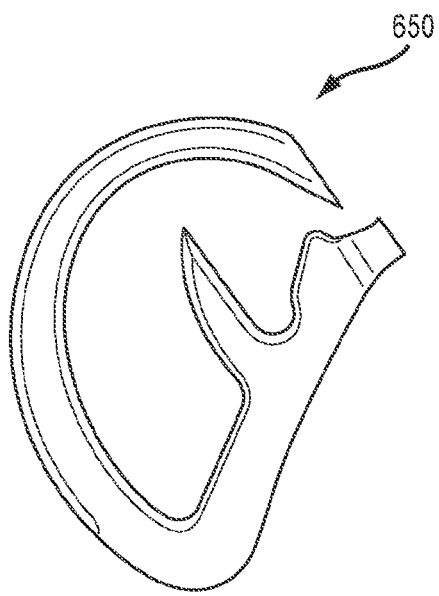
FIG. 35B is a side view of the D-shaped staple in FIG. 35A in a placed configuration.
Figure 35C:
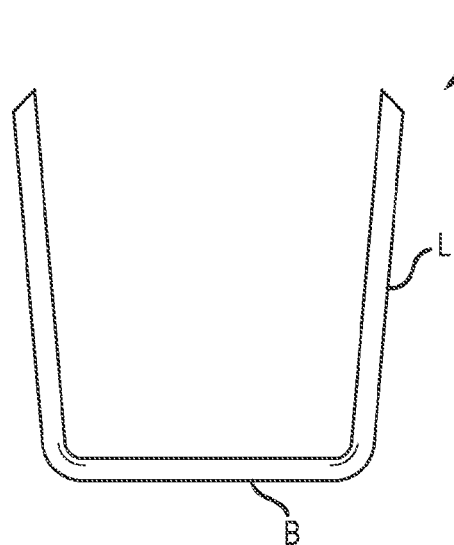
FIG. 35C is a side view of a B-form surgical staple prior to placement.
Figure 35D:
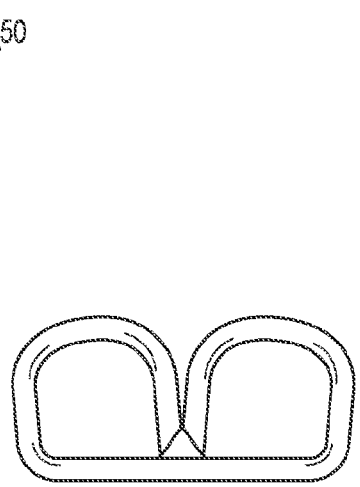
FIG. 35D is a side view of the B-form staple in FIG. 35C in a placed configuration.

In some embodiments, an integrated staple housing providing staples guided by the housing walls as illustrated in FIGS. 5 and/or 29-30 may allow for an increase in wall thickness of the cartridge 508 or housing, and thereby an increased strength of the surgical stapler as compared to staplers in which the pushers may cup the staples. Contrast FIGS. 29-30 with FIGS. 31-32.

In some embodiments, the stapler herein disclosed may be used in a flexible catheter. In some embodiments, the stapler 100 disclosed herein is configured to couple to or to be used with an articulating joint.

As illustrated in FIGS. 20A-20C and/or 33-34, an anchor clamp mechanism 502 or cutting mechanism 108 may provide a safety lock feature. In some embodiments, the mechanism 502, 108 may travel such that that, if too much tissue is clamped (thereby not achieving the necessary gap previously described herein), the mechanism 502, 108 is unable to travel down the anvil 102, and will self-jam, preventing the firing procedure from continuing.

Figure 36:
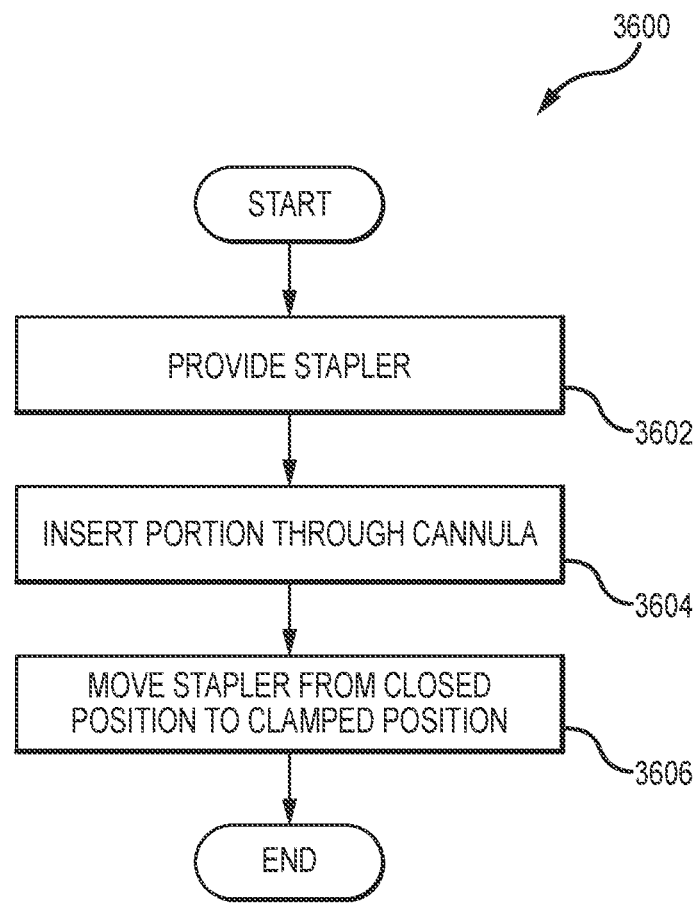
FIG. 36 is a flowchart of an exemplary method.

Turning now to FIG. 36, in some embodiments, a method 3600 of performing a stapling procedure on a patient is provided. The method 3600 may include providing 3602 a surgical stapler in a closed position, inserting 3604 at least a portion of the stapler through a cannula, and moving 3606 the stapler from the closed position to a clamped position.

Providing 3602 a surgical stapler in a closed configuration may include providing a surgical stapler having any of the features previously described herein with reference to FIGS. 1-35B. In some embodiments, providing 3602 includes providing a stapler comprising: an anvil movably coupled to a support jaw; wherein the support jaw comprises a cartridge having an elongated body having a distal end and a proximal end and configured to removably house a plurality of staples. The elongated body may have a first slot shaped to receive a cutting mechanism, a second slot shaped to house at least a first one of the plurality of staples, and a third slot shaped to house at least a second one of the plurality of staples at an angle oblique to the first one of the plurality of staples.

Causing 3604 at least a portion of the surgical stapler to pass through a cannula may include causing at least a portion of the stapler to pass through a cannula having an inner diameter. The cannula may be substantially as previously described herein with reference to FIGS. 1-35B.

Causing 3606 the surgical stapler to move from the closed configuration to the clamped configuration may include causing the stapler to move to a clamped configuration wherein the surgical stapler maintains a gap between the anvil and the support jaw, and the surgical stapler is unable to pass through the cannula. Causing 3606 the stapler to move to the clamped configuration may be achieved using a stapler as previously described with reference to FIGS. 1-35B.

The method 3600 may include stapling tissue using a staple having a leg length of 3.0 mm or more using a stapler configured to pass through a cannula 400 that has an inner diameter of 5.6 mm or less. The method 3600 may include using a stapler that has an envelope diameter of 5.6 mm or less when in a closed position to staple tissue clamped to a thickness that is greater than 1.5 mm.

In some embodiments, the method 3600 further includes longitudinally translating at least one cam to cause at least one of a first staple pusher or a second staple pusher in a direction oblique to the other one of the first staple pusher or the second staple pusher.

In some embodiments, the method 3600 further includes replacing a first cartridge kit in the surgical stapler with a second cartridge kit. The method 3600 may further include using the stapler having the first cartridge kit to place first set of a plurality of staples having a first leg length in a patient, replacing the cartridge kit, and using the stapler having the second cartridge kit to place a second set of a plurality of staples having a second leg length different from the first leg length in a patient. In some embodiments, the same patient receives both sets of staples.

In addition to the description above, various specific examples are disclosed herein.

Example 1: A cartridge for a surgical stapler, comprising: an elongated body configured to fit within an envelope diameter and to removably house a plurality of B-form staples, at least one of the plurality of B-form staples having a base length and a leg length, the leg length at least 53% of the envelope diameter; a first slot shaped to receive a translating cutting mechanism; a second slot shaped to house at least a first one of the plurality of staples; and a third slot shaped to house at least a second one of the plurality of staples at an angle oblique to the first one of the plurality of staples.

Example 2: The cartridge of example 1, further comprising: a curved tissue clamping interface; and wherein the oblique angle is between about 4 degrees and about 30 degrees.

Example 3: The cartridge of example 1 or example 2, wherein: the second slot is shaped to translatably house at least a first staple pusher; the third slot is shaped to translatably house at least a second staple pusher; and the second slot and the third slot are configured to limit the first staple pusher to translation at an angle oblique to translation of the second staple pusher.

Example 4: The cartridge of example 1, wherein: the second slot is shaped to translatably house at least a first staple pusher shaped to support at least the first one of the plurality of staples and a third one of the plurality of staples parallel to the first one of the plurality of staples; the third slot is shaped to translatably house at least a second staple pusher oblique to the first staple pusher, the second staple pusher shaped to support at least the second one of the plurality of staples and a fourth one of the plurality of staples parallel to the second one of the plurality of staples.

Example 5: The cartridge of example any one of the preceding examples, wherein one of: at least one of the plurality of staples has a leg length of 3.42 mm or greater, and the envelope diameter is 5.6 mm or less; or at least one of the plurality of staples has a nominal leg length of 4.72 mm or greater, and the envelope diameter is 8.6 mm or less.

Example 6: The cartridge of example 3 or example 4, wherein: the second slot is shaped to slidably receive a first longitudinally translating cam to effectuate a sliding motion of the first staple pusher; and the third slot is shaped to slidably receive a second longitudinally translating cam to effectuate a sliding motion of the second staple pusher oblique to the sliding motion of the first staple pusher.

Example 7: The cartridge of any one of the preceding examples, wherein: the cartridge comprises a curved tissue clamping interface; and the cartridge is configured to position at least one of the plurality of staples at an angle normal to the curved tissue clamping interface.

Example 8: The cartridge of example 7, wherein: the curved tissue clamping interface is curved about a longitudinal axis extending between a proximal end and a distal end of the elongated body; and the curved tissue clamping interface has a radius of between 40% and 60% of the envelope diameter.

Example 9: The cartridge of example 8, wherein: the envelope diameter is 5.6 mm or less; and at least one of at least the first one of the plurality of staples has a leg length of 3.42 mm or greater; or at least the first one of the plurality of staples is configured to form about tissue clamped to a thickness greater than 1.5 mm.

Example 10: The cartridge of example 1, wherein one of: at least the first one of the plurality of staples has a leg length of 3.42 mm or greater, and the envelope diameter is 5.6 mm or less; or at least the first one of the plurality of staples has a leg length of 4.72 mm or greater, and the envelope diameter is 8.6 mm or less.

Example 11: The cartridge of any one of the preceding examples, wherein:
at least the first one of the plurality of staples is configured to staple about tissue clamped up to a tissue thickness; and the tissue thickness is at least 20% of the envelope diameter.

Example 12: The cartridge of example 11, wherein: the tissue thickness is between about 22% and about 36% of the envelope diameter.

Example 13: The cartridge of example 1, further comprising: a recess for coupling to a cartridge support jaw; and wherein one of the cartridge and the support jaw are shaped to fit within an envelope diameter of 5.6 mm or less; or the cartridge and the support jaw are shaped to fit within an envelope diameter of 8.6 mm or less.

Example 14: The cartridge of example 1, further comprising: a curved tissue clamping interface.

Example 15: The cartridge of any one of the preceding examples, wherein: at least one of the plurality of staples has a leg length that is at least 61% of the envelope diameter.

Example 16: A surgical stapler, comprising: an anvil movably coupled to a support jaw between a clamped configuration wherein the anvil and the support jaw are configured to clamp tissue positioned therebetween, and a closed configuration wherein a tissue clamping interface in the anvil abuts a tissue clamping interface in the cartridge; wherein the support jaw comprises a cartridge having an elongated body configured to removably house a plurality of B-form staples, at least one of the plurality of B-form staples having a base length and a leg length, the cartridge further comprising a first slot shaped to receive a translating cutting mechanism, a second slot shaped to house at least a first one of the plurality of staples, and a third slot shaped to house at least a second one of the plurality of staples at an angle oblique to the first one of the plurality of staples; the anvil and the support jaw comprising the cartridge are shaped to fit within an envelope diameter when in the closed configuration; and the leg length of the at least one of the plurality of B-form staples is at least 53% of the envelope diameter.

Example 17: The stapler of example 16, wherein: the third slot is shaped to house the second one of the plurality of staples at an angle of between about 4 degrees and about 30 degrees relative to the first one of the plurality of staples.

Example 18: The stapler of example 16 or example 17, wherein: the second slot is shaped to translatably house at least a first staple pusher; the third slot is shaped to translatably house at least a second staple pusher; and the second slot and the third slot are configured to limit the first staple pusher to translation at an angle oblique to translation of the second staple pusher.

Example 19: The stapler of example 16, wherein: the second slot is shaped to translatably house at least a first staple pusher shaped to support at least the first one of the plurality of staples and a third one of the plurality of staples parallel to the first one of the plurality of staples; the third slot is shaped to translatably house at least a second staple pusher oblique to the first staple pusher, the second staple pusher shaped to support at least the second one of the plurality of staples and a fourth one of the plurality of staples.

Example 20: The stapler of any one of examples 16-19, wherein one of: at least one of the plurality of staples has a leg length of 3.42 mm or greater, and the envelope diameter is 5.6 mm or less; or at least one of the plurality of staples has a leg length of 4.72 mm or greater, and the envelope diameter is 8.6 mm or less; or the envelope diameter is 5.6 mm or less, and the stapler is configured to staple and cut tissue resulting in a cuff width of greater than 0.5 mm.

Example 21: The stapler of example 19, further comprising: a first longitudinally translating cam; a second longitudinally translating cam positioned oblique to the first longitudinally translating cam; and wherein the second slot is shaped to slidably receive the first longitudinally translating cam to effectuate a sliding motion of the first staple pusher; and the third slot is shaped to slidably receive the second longitudinally translating cam to effectuate a sliding motion of the second staple pusher oblique to the sliding motion of the first staple pusher.

Example 22: The stapler of any one of examples 16-21, further comprising: an expandable cutting mechanism configured to move between a collapsed configuration wherein the cutting mechanism is shaped to fit within the envelope diameter and an expanded configuration wherein the cutting mechanism has a dimension that is greater than the envelope diameter.

Example 23: The stapler of examples 16-21, further comprising: an expandable cutting mechanism having a first member with a cutting portion and a second member; wherein the cutting mechanism is configured to move between a collapsed configuration wherein the cutting portion does not intersect a longitudinal axis defined by the tissue clamping interface of the cartridge and an expanded configuration wherein the cutting portion intersects the longitudinal axis defined by the tissue clamping interface of the cartridge.

Example 24: The stapler of any one of examples 16-23, wherein one of: at least the first one of the plurality of staples has a leg length of 3.42 mm or greater, and the envelope diameter is 5.6 mm or less; or at least the first one of the plurality of staples has a leg length of 4.72 mm or greater, and the envelope diameter is 8.6 mm or less.

Example 25: The surgical stapler of example 16 or example 24, wherein: the surgical stapler is configured to staple and cut tissue up to a pre-defined tissue thickness; the tissue thickness is defined as a distance between the anvil and the cartridge during stapling; and the tissue thickness is at least 20% of the envelope diameter when the stapler is in the closed configuration.

Example 26: The stapler of any one of examples 16-25, wherein: the anvil has a curved tissue clamping interface; and the cartridge has a curved tissue clamping interface shaped to engage the curved tissue clamping interface of the anvil when the stapler is in the closed configuration.

Example 27: The stapler of any one of examples 16-26, wherein: at least one of the plurality of staples has a leg length that is at least 61% of the envelope diameter.

Example 28: A method of placing a surgical staple in a patient, comprising: providing a surgical stapler in a closed configuration, the stapler comprising an anvil movably coupled to a support jaw between a clamped configuration wherein the anvil and the support jaw are configured to clamp tissue positioned therebetween, and a closed configuration wherein a tissue clamping interface in the anvil abuts a tissue clamping interface in the cartridge, wherein the support jaw comprises a cartridge configured to removably house a plurality of B-form staples, at least one of the plurality of B-form staples having a base length and a leg length, the cartridge further comprising a first slot shaped to receive a translating cutting mechanism, a second slot shaped to house at least a first one of the plurality of staples, and a third slot shaped to house at least a second one of the plurality of staples at an angle oblique to the first one of the plurality of staples, the anvil and the support jaw comprising the cartridge are shaped to fit within an envelope diameter when in the closed configuration, and the leg length of the at least one of the plurality of B-form staples is at least 53% of the envelope diameter; passing at least a portion of the stapler in the closed configuration through an envelope diameter; positioning tissue between the anvil and the support jaw; moving the anvil to the clamped configuration wherein the anvil and the support jaw clamp the tissue; and causing the stapler to form the plurality of staples about the tissue.

Example 29: The method of example 28, further comprising: housing a third one of the plurality of staples parallel to the first one of the plurality of staples; and housing a fourth one of the plurality of staples parallel to the second one of the plurality of staples; and wherein one of the surgical stapler has an envelope diameter of 5.6 mm or less; or the surgical stapler has an envelope diameter of 8.6 mm or less.

Example 30: The method of example 28, further comprising: clamping tissue between a curved tissue clamping interface in the support jaw and a curved tissue clamping interface in the anvil.

Example 31: A surgical stapler, comprising: an anvil movably coupled to a support jaw between a clamped configuration wherein the anvil and the support jaw are configured to clamp tissue positioned therebetween, and a closed configuration wherein a tissue clamping interface in the anvil abuts a tissue clamping interface in the cartridge, the anvil and the support jaw defining an envelope diameter when the anvil is in the closed configuration; and a translating cutting mechanism having a first member having a cutting portion, and a second member, the cutting mechanism movable between a collapsed configuration wherein the cutting mechanism is shaped to fit within the envelope diameter and an expanded configuration wherein the cutting mechanism does not fit within the envelope diameter; wherein the support jaw comprises a cartridge having a first slot shaped to receive the translating cutting mechanism, a second slot shaped to house at least a first one of the plurality of staples, and a third slot shaped to house at least a second one of the plurality of staples.

Example 32: The surgical stapler of example 31, wherein: at least one of the first member or the second member has at least one guide, the at least one guide configured to engage a corresponding guide on the anvil to limit the cutting mechanism to translation relative to the corresponding guide.

Example 33: The surgical stapler of example 31 or example 32, wherein one of: the envelope diameter is 5.6 mm or less; or the envelope diameter is 8.6 mm or less.

Example 34: The surgical stapler any one of examples 31-33, further comprising: a first actuator coupled to the first member, the first member configured to move the first member distally and onto the anvil; and a second actuator coupled to the second member, the actuator configured to move the second member distally and onto the support jaw.

Example 35: The surgical stapler of example 34, wherein: the first actuator comprises a flexible member.

Example 36: The surgical stapler of any one of examples 31-35, wherein: the first member comprises at least one leg having a first flange; and the second member comprises at least one leg having a second flange, the first flange and the second flange shaped to limit expansion of the cutting mechanism.

Example 37: The surgical stapler of any one of examples 31-36, wherein: the cutting mechanism is configured to compress the anvil and the support jaw towards each other and into the clamped configuration as the cutting mechanism translates towards a distal end of the surgical stapler.

Example 38: The surgical stapler of any one of examples 31-37, wherein: the stapler has an envelope diameter of 5.6 mm in the closed configuration, and is configured to staple and cut tissue clamped between the anvil and the support jaw such that the cut tissue has a cuff width of greater than 0.5 mm.

Each of the various elements disclosed herein may be achieved in a variety of manners. This disclosure should be understood to encompass each such variation, be it a variation of an embodiment of any apparatus embodiment, a method or process embodiment, or even merely a variation of any element of these. Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled.

As but one example, it should be understood that all action may be expressed as a means for taking that action or as an element which causes that action. Similarly, each physical element disclosed should be understood to encompass a disclosure of the action which that physical element facilitates. Regarding this last aspect, by way of example only, the disclosure of a clamp should be understood to encompass disclosure of the act of clamping—whether explicitly discussed or not—and, conversely, were there only disclosure of the act of clamping, such a disclosure should be understood to encompass disclosure of a "clamping mechanism". Such changes and alternative terms are to be understood to be explicitly included in the description.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A surgical stapler, comprising:
an anvil movably coupled to a support jaw between a clamped configuration wherein the anvil and the support jaw are configured to clamp tissue positioned therebetween, and a closed configuration; wherein
the support jaw comprises a cartridge having an elongated body configured to removably house a plurality of B-form staples,
at least one of the plurality of B-form staples having a base and a leg,
the cartridge further comprising a first slot shaped to receive a translating cutting mechanism, a second slot shaped to house at least a first one of the plurality of staples, and a third slot shaped to house at least a second one of the plurality of staples at an angle oblique to the first one of the plurality of staples;
the anvil and the support jaw comprising the cartridge are shaped to fit within an envelope diameter when in the closed configuration; and
an expandable cutting mechanism having a cutting portion coupled to a first movable member, the cutting mechanism configured to move between a collapsed configuration wherein the cutting mechanism is shaped to fit within the envelope diameter and an expanded configuration wherein at least a portion of the first movable member is exterior of the envelope diameter.

2. The stapler of claim 1, wherein:
the third slot is shaped to house the second one of the plurality of staples at an angle of between about 4 degrees and about 30 degrees relative to the first one of the plurality of staples.

3. The stapler of claim 1, wherein:
the second slot is shaped to translatably house at least a first staple pusher;
the third slot is shaped to translatably house at least a second staple pusher; and
the second slot and the third slot are configured to limit the first staple pusher to translation at an angle oblique to translation of the second staple pusher.

4. The stapler of claim 1, wherein:
the second slot houses at least a first staple pusher and the first one of the plurality of staples; wherein
the first pusher is shaped to position the base of the first one of the plurality of staples in contact with the elongated body.

5. The stapler of claim 4, wherein one of:
the first staple pusher is shaped to maintain the base of the first one of the plurality of staples in contact with the elongated body as the first one of the plurality of staples is translated relative to the elongated body.

6. The stapler of claim 1, further comprising:
an upper anvil positioner and a lower anvil positioner, the lower anvil positioner having at least one flange shaped to engage the anvil to effectuate movement of the anvil to the closed configuration, an open configuration, and the clamped configuration.

7. The stapler of claim 1, wherein:
the cutting mechanism further comprises a second movable member;
the first and second movable members are movable in a longitudinal direction; and
at least one of the first or second movable members is rotatable relative to the other one of the first or second movable members.

8. The stapler of claim 1, wherein:
when the cutting mechanism is in the collapsed configuration and the anvil is in the clamped configuration, an uppermost surface of the cutting mechanism is below an uppermost surface of the anvil; and
when the cutting mechanism is in the expanded configuration, the uppermost surface of the cutting mechanism is above the uppermost surface of the anvil.

9. The stapler of claim 1, wherein:
at least the first one of the plurality of staples has a leg length of 3.42 mm or greater, and the envelope diameter is 5.6 mm or less.

10. The surgical stapler of claim 1, wherein:
the surgical stapler is configured to maintain a gap between the anvil and the jaw when in the clamped configuration; and
the gap is 13% of the envelope diameter or greater.

11. The stapler of claim 1, wherein:
the anvil has a curved tissue clamping interface; and
the cartridge has a curved tissue clamping interface shaped to engage the curved tissue clamping interface of the anvil when the stapler is in the closed configuration.

12. The stapler of claim 1, wherein:
at least one of the plurality of staples has a leg length that is at least 53% of the envelope diameter.

13. The stapler of claim 1, wherein:
the elongated body has a first side with a tissue clamping interface and a second side; and
the first slot passes through the first side and the second side.

* * * * *